(12) United States Patent
 Jewell

(10) Patent No.: US 11,808,748 B2
(45) Date of Patent: Nov. 7, 2023

(54) RADON DETECTION DEVICES AND METHODS

(71) Applicant: FORMATIVE HOLDINGS, LLC, Murray, UT (US)

(72) Inventor: Travis A. Jewell, Tyler, TX (US)

(73) Assignee: FORMATIVE HOLDINGS, LLC, Murray, UT (US)

( * ) Notice: Subject to any disclaimer, the term of this patent is extended or adjusted under 35 U.S.C. 154(b) by 417 days.

(21) Appl. No.: 16/808,129

(22) Filed: Mar. 3, 2020

(65) Prior Publication Data
US 2020/0284776 A1 Sep. 10, 2020

Related U.S. Application Data

(60) Provisional application No. 62/813,614, filed on Mar. 4, 2019, provisional application No. 62/871,613, filed on Jul. 8, 2019.

(51) Int. Cl.
*G01N 33/00* (2006.01)
*G01N 1/22* (2006.01)
(Continued)

(52) U.S. Cl.
CPC ....... *G01N 33/0055* (2013.01); *G01N 1/2273* (2013.01); *G01T 1/16* (2013.01);
(Continued)

(58) Field of Classification Search
CPC .................................................. G01N 33/0055
See application file for complete search history.

(56) References Cited

U.S. PATENT DOCUMENTS 3,089,032 A 5/1963 Goupil et al.
4,432,248 A * 2/1984 Lalin .................... G01N 1/2273
73/864.34

(Continued)

FOREIGN PATENT DOCUMENTS

CN 206096475 U * 4/2017
CN 108662245 A * 10/2018 ............. F16K 31/04
(Continued)

OTHER PUBLICATIONS

Janik, M., et al. "Determination of the minimum measurement time for estimating long-term mean radon concentration." Radiation protection dosimetry 152.1-3 (2012): 168-173 (Year: 2012).*
(Continued)

*Primary Examiner* — Kristina M Deherrera
*Assistant Examiner* — Fatemeh Esfandiari Nia
(74) *Attorney, Agent, or Firm* — MASCHOFF BRENNAN

(57) ABSTRACT

A method of detecting radon may include starting a first timer at a radon detection device in response to a first triggering action. A seal of the radon detection device may transition to a seal position from an open position in response to the first timer being equal to a measurement interval. The open position may facilitate the introduction of ambient air to a vent of the radon detection device. The seal position may discourage introduction of the ambient air to the vent. The vent may be in fluid communication with a test material. The test material may collect radon from the ambient air introduced to the radon detection device. A second timer may be started in response to the seal transitioning from the open position to the seal position. The seal remains in the sealed position following the transition from the open position to the sealed position.

17 Claims, 26 Drawing Sheets

(51) Int. Cl.
    *G01T 1/17*    (2006.01)
    *G01T 1/167*   (2006.01)
    *G01T 1/16*    (2006.01)
    *G01T 1/178*   (2006.01)
(52) U.S. Cl.
    CPC ............ *G01T 1/167* (2013.01); *G01T 1/17* (2013.01); *G01T 1/178* (2013.01)

(56) References Cited

U.S. PATENT DOCUMENTS

| | | | |
|---|---|---|---|
| 5,107,108 A * | 4/1992 | Ramsey | G01T 1/178 250/DIG. 2 |
| 2005/0183940 A1* | 8/2005 | Ichimaru | E05F 1/1066 200/523 |
| 2009/0230305 A1 | 9/2009 | Burke et al. | |
| 2017/0160402 A1 | 6/2017 | Yoshioka et al. | |
| 2018/0143106 A1* | 5/2018 | Byström | G01T 1/178 |
| 2018/0224562 A1 | 8/2018 | Jewell et al. | |
| 2019/0365608 A1* | 12/2019 | Lewis | G16H 40/63 |
| 2020/0056793 A1* | 2/2020 | Etemadi | F23N 5/245 |

FOREIGN PATENT DOCUMENTS

| | | |
|---|---|---|
| CN | 108663704 A | 10/2018 |
| CN | 107219549 A | 6/2019 |
| KR | 101040073 B1 | 6/2011 |
| KR | 20150072742 A | 6/2015 |

OTHER PUBLICATIONS

CN-108662245-A—English (Year: 2018).*
Canadian Intellectual Property Office; Office Action issued in CA Application No. 3,123,636 dated Dec. 1, 2022; 3 pages.
European Patent Office; Extended European Search Report issued in EP Application No. 20766962.3 dated Sep. 9, 2022; 12 pages.

* cited by examiner

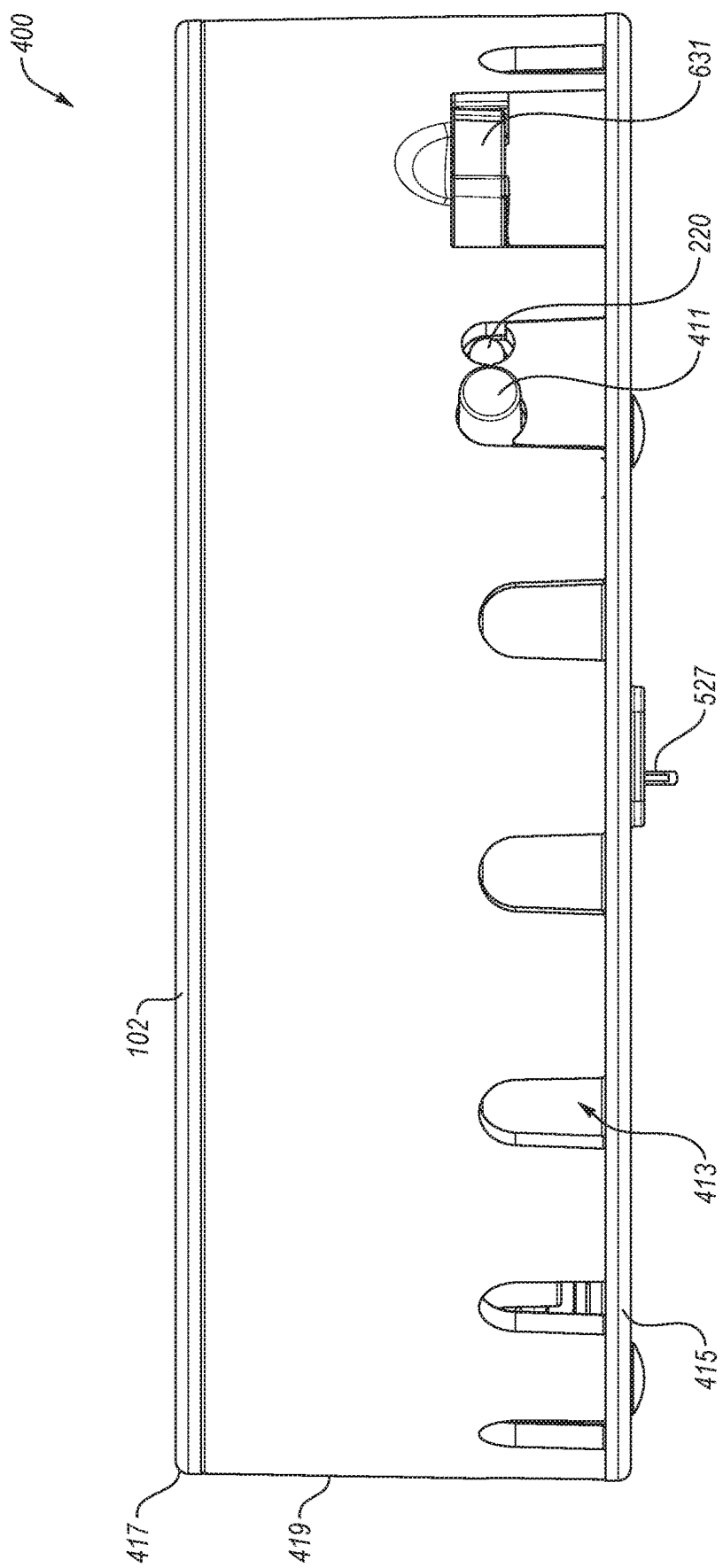

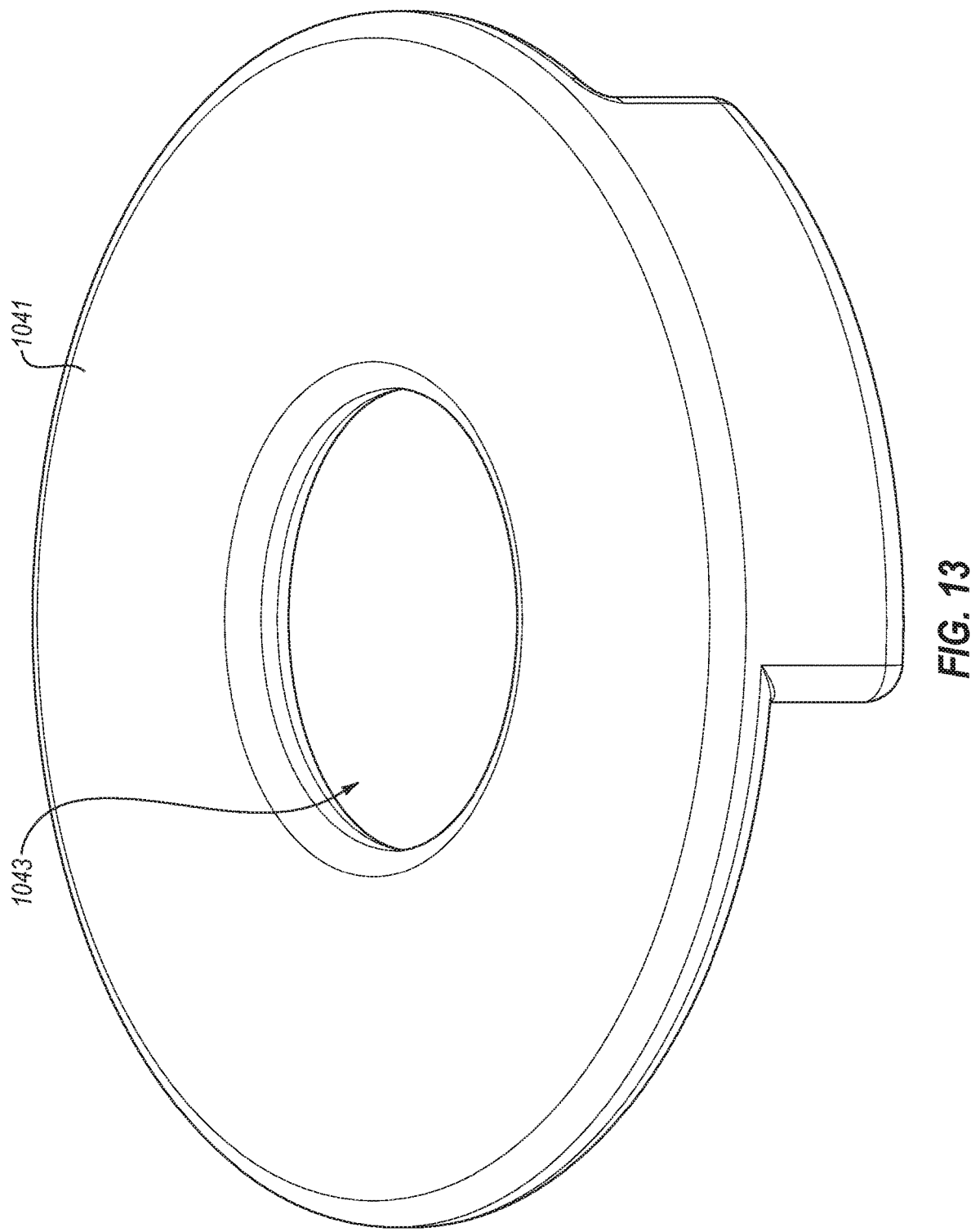

RADON DETECTION DEVICES AND METHODS

CROSS-REFERENCE TO RELATED APPLICATIONS

This application claims the benefit of and priority to U.S. Provisional Patent App. No. 62/813,614, filed Mar. 4, 2019 and U.S. Provisional App. No. 62/871,613, filed Jul. 8, 2019, both of which are incorporated herein by reference.

FIELD

The embodiments discussed in the present disclosure are related to radon detection devices. In particular, some embodiments relate to low cost mechanical radon detection devices and implementations thereof.

BACKGROUND

Radon gas is an invisible, odorless, naturally occurring radioactive gas that is created by the radioactive decay chain of Uranium. As Uranium decays, it becomes radium and radium decays to become radon gas. A form of radon gas, radon 222 gas, seeps out of the soil and into the atmosphere where it dilutes to small percentage in the air. In this process, some of the radon gas enters homes and/or buildings via the foundation or by water that is present in the soil surrounding the foundation.

Radon gas is dangerous when inhaled into the lungs of individuals living and working in homes and/or buildings in which radon 222 has seeped. As inhaled radon gas decays, it becomes several other radon decay products that decay until becoming lead 206. Additionally, as radon decays, alpha radiation is released that can damage the tissue in lungs. Such damage can cause mutations that can eventually become cancerous. The health risks associated with Radon gas increase as the exposure amount increases and as a time of exposure increases.

Radon 222 gas in air is categorized as a group-1 carcinogen by the American Cancer Society. According to the United States Environmental Protection Agency (USEPA), radon 222 gas is the second leading cause of lung cancer causing greater than 20,000 deaths annually. The USEPA recommends that people take action to reduce exposure to radon levels greater than four picocuries per liter. The World Health Organization recommends that people take meditative action to reduce exposure to radon gas levels greater than 2.7 picocuries per liter.

Radon gas occurs throughout the world in varying degrees. Although some areas are geologically less susceptible to radon gas, it can be a problem anywhere. Neighboring buildings can have radon levels of significant difference due to geology, source, ventilation and construction qualities of each building.

Because radon gas is a known risk, people around the world are taking action to test for radon gas and to prevent exposure to it. Because radon gas is odorless, colorless, tasteless and inert, the only way to detect its presence is by performing a radon test using a radon detection device. Screening is the only way to reduce radon risk and there is a need for improved screening methods.

The subject matter claimed in the present disclosure is not limited to embodiments that solve any disadvantages or that operate only in environments such as those described above. Rather, this background is only provided to illustrate one example technology area where some embodiments described in the present disclosure may be practiced.

SUMMARY

This Summary introduces a selection of concepts in a simplified form that are further described below in the Detailed Description. This Summary is not intended to identify key features or essential characteristics of the claimed subject matter, nor is it intended to be used as an aid in determining the scope of the claimed subject matter.

In an example embodiment, a method of detecting radon may include starting a first timer at a clock circuit of a radon detection device in response to a first triggering action. A seal of the radon detection device may be transitioned to a seal position from an open position in response to the first timer being substantially equal to a measurement interval. The open position may facilitate the introduction of ambient air to a vent of the radon detection device. The seal position may discourage introduction of the ambient air to the vent. The vent may be in fluid communication with a test material located within the radon measurement device. The test material may be configured to collect radon from the ambient air introduced to the radon detection device. A second timer may be started in response to the seal transitioning from the open position to the seal position. The seal remains in the sealed position following the transition from the open position to the sealed position.

Additional features and advantages will be set forth in the description which follows, and in part will be obvious from the description, or may be learned by practice. The features and advantages may be realized and obtained by means of the instruments and combinations particularly pointed out in the appended claims. These and other features will become more fully apparent from the following description and appended claims.

BRIEF DESCRIPTION OF THE DRAWINGS

Example embodiments will be described and explained with additional specificity and detail through the use of the accompanying drawings in which:

FIG. 4B illustrates a side view of the example radon detection device;

FIG. 13 illustrates a perspective view of test material that may be implemented in the radon detection device of FIGS. 4A-4C;

DESCRIPTION OF SOME EXAMPLE EMBODIMENTS

Figure 1:
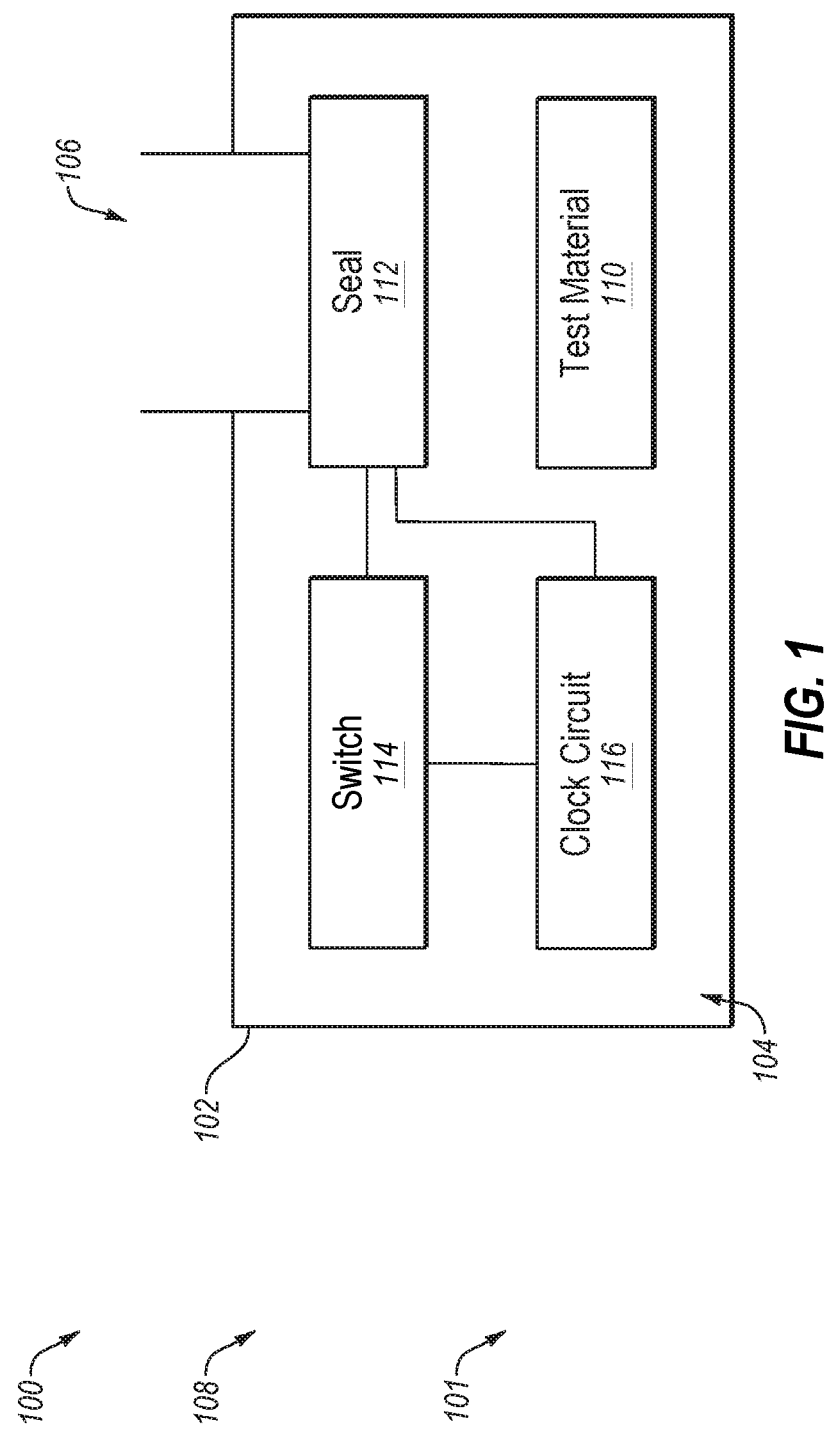
FIG. 1 illustrates a block diagram of an example radon detection device.

Current technologies offer radon measurements at varying cost, informational, and duration levels. However, current technologies are problematic and can provide end-users with inaccurate data causing them to either be exposed to more radon than reported, which may increase their lung cancer risk or impact a user investment decision on expensive radon abatement equipment.

Professional radon measurement providers usually belong to a certification organization or government licensing program. Professionals are hired by end users to provide radon gas measurements in structures such as homes, schools, government buildings, and commercial buildings. Professional radon measurement providers are usually for-profit entities. The professional measurements require a professional to travel to the site, deploy a measurement device, and return after a period of time to retrieve the measurement device. After the measurement device is retrieved, data indicative of radon levels may be accessed and a report may be generated based on the accessed data. The report show hourly radon levels. From the hourly radon levels, an average radon concentration may be calculated. An owner of the structure may base an abatement system on the average radon concentration.

Another option that provides a more economical option to determine an Average Radon Level in a structure may include passive radon detection devices. In the passive radon detection devices, activated charcoal, liquid scintillation (e.g., test materials), charged-electric passive devices, and alpha-track devices are most commonly used. The passive radon detection devices may be long-term, passive radon measurement devices. Long-term, passive radon measurement devices may be implemented for a period over a few months. For instance, the period may be between about 90 days and about one year.

The passive radon detection devices may also include short-term single use measurement devices that can be used by non-professionals and professionals. The duration of the short-term radon test may range from about twenty-four hours up to about seven days. The user follows the instructions that include the national standards for placing a passive radon detection device. After the passive radon detection device has been exposed to ambient air in the structure for the duration specified in the instructions (e.g., a measurement interval), the radon test is completed by sealing a radon measurement devices such as a diffusion chamber of the passive radon detection device to stop exposure of the test materials to the ambient air.

The user then packages the passive radon detection device, the test materials, or both and ships it to the lab for analysis. The shipping transit can be a long period of time before being received by the lab. Once the lab receives the package, the lab measures the radon decay products in the test materials and calculate the quantities vs the time the test material was exposed to the ambient air to determine the radon concentration. The lab provides a single number which is the Average Radon Level. The single number is provided because the test material does not allow hourly readings. Thus, lab results based on passive detection device test materials include a margin of error estimated by factors that can be derived from shipping time, over-exposure, vapor content or other factors that can affect radon absorption and/or measurement.

An issue with previous passive radon detection devices may be that the user is expected to record vital information regarding the testing process. For example, the user may be expected to complete a vital information card that includes fields for the exact time the test material was exposed and the exact time the radon measurement devices was sealed to stop exposure of the test material to the ambient air. Some users may inaccurately record or fail to verify the times when the test material was exposed or when the radon measurement devices was sealed.

Another issue with previous passive radon detection devices may be that the user may not properly monitor the passive radon detection devices during the radon test and the test materials may be exposed for too short or too long of a period of time. If the times that the test material was exposed, the radon measurement device was sealed, or both are inaccurately recorded, the results may be affected. For example, if the test material was exposed for an extra day than recorded, the Average Radon Level indicated in the results may be higher than it should be. Additionally, the user may improperly start exposing the test material or seal the radon measurement device, which may over expose or under expose the test material. For example, the user may seal the radon measurement device on a date that is actually prior to the date that is recorded.

Furthermore, inaccurately recording when the radon measurement device is sealed may impact the margin of error estimated by the lab. For example, if the shipping time was actually longer than recorded (e.g., the user recorded a later date or time than when the radon measurement device was actually sealed), the margin of error used to account for the shipping time may be incorrect and the Average Radon Level indicated in the results may also be incorrect.

Additionally, a user may be financially motivated to tamper with the radon test to ensure that the Average Radon Level is substantially equal to or below an acceptable threshold. For example, a user may be trying to sell a house and to ensure that the Average Radon Level is substantially equal to or below the acceptable threshold for selling the house without performing abatement services, the user may move the passive radon detection device, seal the radon measurement device early, or both. Additionally, the user or someone else visiting the house (e.g., during a showing) may inadvertently move the passive radon detection device. Likewise, physically moving the passive radon detection device may change a humidity level, a temperature, and other environmental factors of the ambient air.

Accordingly, some embodiments described in the present disclosure provide users with an economical solution to current technology problems. These embodiments provide solutions to user error, shipping problems, and tamper problems that exist with existing technologies. For example, some embodiments create a means to provide passive radon detection devices that are self-timed to seal the radon measurement device and configured to automatically record the date and time of key steps in the radon test (e.g., when the test material is first exposed to the ambient air and when the radon measurement device is sealed). Additionally, some embodiments described in the present disclosure may provide a notification that a measurement interval has elapsed and that the radon measurement device has been sealed to reduce the shipping time. Likewise, some embodiments described in the present disclosure may provide tamper detection devices to determine if the passive radon detection devices are tampered with during the measurement interval.

These and other embodiments of the present disclosure will be explained with reference to the accompanying figures. In the figures, features with like numbers indicate like structure and function unless described otherwise.

FIG. 1 illustrates an example radon detection device 100 (referred to in the present disclosure as "device 100"). The device 100 may be configured to collect radon gas in ambient air 108 of an environment 101 (e.g., an external environment) to permit a lab to determine an Average Radon Level on the ambient air 108. The device 100 may be configured to be in a sealed configuration or an open configuration. In the sealed configuration, the device 100 may prevent the ambient air 108 from entering a radon measurement device 104 that may be at least partially defined by a housing 102 of the device 100.

The radon measurement device 104 may include a diffusion chamber in some embodiments. In these and other embodiments, the diffusion chamber may include two volumes separated by a filter. Nuclear track detectors may be placed inside the volumes to detect alpha particles of radon and/or its progenies. In other embodiments, the radon measurement device 104 may include a carbon or charcoal-based detection device (e.g., a charcoal canister, charcoal liquid scintillation, etc.). In yet other embodiments, the radon measurement device 104 may include an alpha-track detector.

In the open configuration, the device 100 may permit the ambient air 108 to enter the radon measurement device 104 via a vent 106 defined by the housing 102. FIG. 1 depicts the device 100 in the sealed configuration, which may occur before a switch 114 transitions from a first position to a second position or after the switch 114 transitions from a lock position to the first position as described below. The switch 114 being in the first position may cause a seal 112 to be in a seal position (e.g., positioned proximate the vent 106). The seal 112 being in the seal position may hermetically seal the radon measurement device 104.

In some embodiments, the device 100 may be configured to reduce or eliminate user error and to impart regularity and reliability in exposure of a test material 110 disposed in the radon measurement device 104 to the ambient air 108 for a particular measurement interval. The ambient air 108 may be within a structure such as a house or a building (e.g., the environment 101). For example, the ambient air 108 may be within a basement of a house.

The ambient air 108 may include radon gas. The test material 110 may be configured to collect the radon gas or decay products of radon in the ambient air 108 that the test material 110 is exposed to such that a lab may determine an Average Radon Level of the ambient air 108. In some embodiments, the test material 110 may include activated charcoal, liquid scintillation, or any other appropriate material. The test material 110 being erroneously exposed to the ambient air 108 prior to or after the measurement interval may skew the Average Radon Level. Based on the Average Radon Level, a user such as an owner or manager of the structure may abate or mitigate the radon gas.

To deploy the device 100, a user may place the device 100 in the environment 101. Additionally, the user may impose triggering actions on the switch 114. The triggering actions may cause the switch 114 to change positions and cause the seal 112 to transition between the open position and the seal position. Concurrently, the triggering actions may cause functions of a clock circuit 116 to be initiated. For example, the triggering actions may begin one or more timers determined by the clock circuit 116. As used in the present disclosure, concurrent or substantially concurrent may include simultaneous, immediately following, or without material delay, such as a fraction of a second (e.g., 0.5 seconds or less). Hereinafter in the present disclosure, "concurrently or substantially concurrently" is referred to as "concurrently."

In this and other embodiments, the clock circuit 116 may include or may be replaced by a mechanical timer. For instance, the first timer of the clock circuit 116 may be performed by a mechanical timer. The mechanical timer may include, for example, a spring wound timer. The mechanical timer may be preset such that the triggering actions initiate the mechanical timer without input from the user. Alternatively, the user may prepare the mechanical time (e.g., the user may wind a spring that drives the mechanical timer).

To initiate exposure of the test material 110 to the ambient air 108, a first triggering action may be imposed on the switch 114 (e.g. the switch 114 may be moved from the first position to the second position). The seal 112 may be configured such that responsive to the first triggering action, the seal 112 may concurrently transition to the open position from the seal position and the radon measurement device 104 may be fluidly connected with the ambient air 108 via the vent 106. Likewise, the first triggering action may cause the clock circuit 116 to initiate a first timer. The first timer may indicate a total amount of time the test material 110 has currently been exposed or was exposed to the ambient air 108 (e.g., a first time period). The first timer may be representative of a period of time since the seal 112 transitioned to the open position from the seal position.

To increase the likelihood that the test material 110 is exposed to the ambient air 108 for the particular measurement interval, a second triggering action may be imposed on the switch 114 (e.g., the switch 114 may be moved from the second position to the lock position). The switch 114 being in the lock position may cause the seal 112 to be locked in the open position until the first timer is substantially equal to the measurement interval. In other words, the switch 114 being in the lock position may prevent the seal 112 from transitioning to the seal position from the open position prior to exposing the test material 110 to the ambient air 108 for an amount of time substantially equal to the measurement interval. For example, if the measurement interval is forty eight hours and the first triggering action and the second triggering action occurred concurrently at substantially eight AM on a Monday, the switch 114 may be locked in the lock position until substantially eight AM on a following Wednesday.

Likewise, to prevent the test material 110 from being exposed to the ambient air 108 for more time than the measurement interval, a third triggering action may be imposed on the switch 114 (e.g., the switch 114 may be moved from the lock position to the first position). The seal 112 may be configured such that responsive to the third triggering action being imposed on the switch 114, the seal 112 may be concurrently affected such that the vent 106 is sealed to prevent the ambient air 108 from entering the radon measurement device 104. Similarly, in these and other embodiments, the second triggering action may result in a similar change of state of an apparatus or system that is configured to close and/or seal the vent 106. For instance, the second triggering action may cause a change in state of a device relative to an aperture. The device may close and seal the aperture to isolate the device 100 from the environment 101. In other embodiments, another suitable system or apparatus may be implemented to close the vent 106.

In addition, the third triggering action may cause the clock circuit 116 to initiate a second timer and/or stop the first timer. The second timer may indicate an amount of time since the seal 112 transitioned to the seal position from the open position (e.g., a second time period or a current amount of shipping time). Likewise, stopping the first timer may record an actual amount of time the test material 110 was exposed to the ambient air 108. With the seal 112 in the seal position, the radon measurement device 104 may be substantially hermetically sealed. In some embodiments, the seal 112 may include one or more of a spring loaded gasket and a diaphragm.

In some embodiments, exposure of the test material 110 to the ambient air 108 may start when the switch 114 transitions to the second position from the first position. Alternatively, in some embodiments, exposure of the test material 110 to the ambient air 108 may start when the switch 114 transitions to the lock position. In these and other embodiments, the switch 114 may transition from the first position to the second position and subsequently to the lock position concurrently. Concurrent transition of the switch 114 to the lock position may maintain the seal 112 in the open position for the duration of the measurement interval. In some embodiments, the second position and the lock position may be the same and the switch 114 may be configured to transition between just the first position and the lock position.

The triggering actions initiating the timers of the clock circuit 116 may ensure that the radon test is performed properly. Because the initiation of the timers occurs concurrently with the triggering actions, determination of the first timer being substantially equal to the measurement interval may be reliable. That is, the test material 110 may not be exposed to the ambient air 108 prior to the first triggering action or after the third triggering action (e.g., the test material 110 may not be exposed to the ambient air 108 for more time than the amount of time included in the measurement interval).

The clock circuit 116 may be communicatively coupled to the switch 114. The clock circuit 116 may be configured to generate time data. The time data may include a global time (e.g., a current time), the first timer, and the second timer. In some embodiments, the clock circuit 116 may be configured to cause the switch 114 to transition between the first position, the second position, and the lock position. For example, when the first timer is substantially equal to the measurement interval, the clock circuit 116 may cause the switch 114 to transition from the lock position to the first position (e.g., the clock circuit 116 may provide the third triggering action automatically to cause the seal 112 to transition to the seal position).

In some embodiments, the clock circuit 116 may be communicatively coupled to the seal 112. In these and other embodiments, the clock circuit 116 may initiate and/or stop the first timer and the second timer based on the seal 112 transitioning between the seal position and the open position. For example, the clock circuit 116 may initiate the first timer based on the seal 112 transitioning from the seal position to the open position. Additionally, the clock circuit 116 may end the first timer and/or start the second timer based on the seal 112 transitioning from the open position to the seal position.

In some embodiments, the switch 114, after the third triggering action, may be configured to prevent the seal 112 from transitioning from the seal position back to the open position. Thus, the switch 114 may prevent the test material 110 from being exposed to the ambient air 108 for a period of time beyond the measurement interval. Alternately or additionally, the seal 112 may be configured such that the seal 112 may not transition from the closed position to the open position more than once. For instance, the seal 112 may be configured to transition from the closed position to the open position only in response to the first triggering action and may lack the ability to transition from the closed position to the open position following the third triggering action.

The device 100, after the third triggering action, may be sent to a lab to obtain the results of the radon test. For example, the Average Radon Level of the ambient air 108 may be calculated based on an amount of radon decay products collected by the test material 110, which may be used to recommend or size an abatement system for the environment 101. In some embodiments, the lab may verify that that first timer was substantially equal to the measurement interval to properly calculate the Average Radon Level. Additionally, in some embodiments, the lab may use the second timer (e.g., the shipping time) to determine a proper margin of error for calculating the Average Radon Level.

The housing 102 may be comprised of a plastic, a metal, or another suitable material. The housing 102 may define the vent 106 as an opening in the housing 102 formed such that the ambient air 108 may enter the radon measurement device 104 via the vent 106. In some embodiments, the vent 106 may be defined as a single opening or multiple openings. In some embodiments, the vent 106 may be defined such that the vent 106 is defined by a portion of a sidewall of the housing 102. In other embodiments, the vent 106 may be defined such that the vent 106 is substantially defined by an entire sidewall of the housing 102 (e.g., the vent 106 may include multiple openings in the sidewall). Additionally, the vent 106 may be defined as a single vent 106 in a single sidewall of the housing 102 or as multiple vents 106 in multiple sidewalls of the housing 102.

The clock circuit 116 may be configured to limit the exposure of the test material 110 to the ambient air 108 to just the measurement interval. In some embodiments, the measurement interval may be configurable by a user of the device 100. For example, the measurement interval may include at least one of 24 hours, 48 hours, 72 hours, and 96 hours and up to a year following the first triggering action.

In some embodiments, the first triggering action, the second triggering action, the third triggering action, or any combination thereof may be performed by the user. In other embodiments, the first triggering action, the second triggering action, and the third triggering action may be performed in part by the user and in part by the device 100. For example, in some embodiments, the second triggering action and the third triggering action may be performed automatically by the clock circuit 116 or another device configured to cause the switch 114 to transition to the second position, the lock position, or both in response to the first timer being substantially equal to the measurement interval.

In these and other embodiments, the first triggering action may occur some predetermined time from a preliminary action. For instance, the user may take a preliminary action, which may set into motion the first triggering action, the second triggering action, etc. The predetermined time may enable the user to situate an environment or the device 100. For example, the preliminary action may be taken by the user. The predetermined time may be 1 hour, 2 hours, 3 hours, 24 hours, or another suitable time. During the predetermined time, the user may close windows, adjust the HVAC, exit the facility, etc. Following the predetermined time, the first triggering action may occur to commence the monitoring. The preliminary action may enable a more accurate monitoring. For instance, the preliminary action may prevent measurement of moving air when the user leaves the structure or from an HVAC vent left on during an initial stage of the test.

In some embodiments, the switch 114 may be disposed within the radon measurement device 104. In these and other embodiments, the device 100 may include an initiation button (not illustrated) configured to cause the switch 114 to transition to the second position and the lock position. In other embodiments, the switch 114 may be positioned external to the radon measurement device 104. For example, the switch 114 may be positioned on an external surface of the housing 102. Alternatively, the housing 102 may include at least a portion of the switch 114. For example, the housing may include multiple portions with one or more of the portions of the housing 102 being configured to move independent of or relative to the other portions of the housing 102.

Modifications, additions, or omissions may be made to the device 100 without departing from the scope of the present disclosure. The present disclosure applies to the device 100 including various combinations of components (e.g., 110, 112, 114, 116, etc.) and different numbers of such components. Moreover, the separation of various components in the embodiments described in the present disclosure is not meant to indicate that the separation occurs in all embodiments. Moreover, it may be understood with the benefit of this disclosure that the described components may be integrated together in a single component or separated into multiple components.

Figure 2:
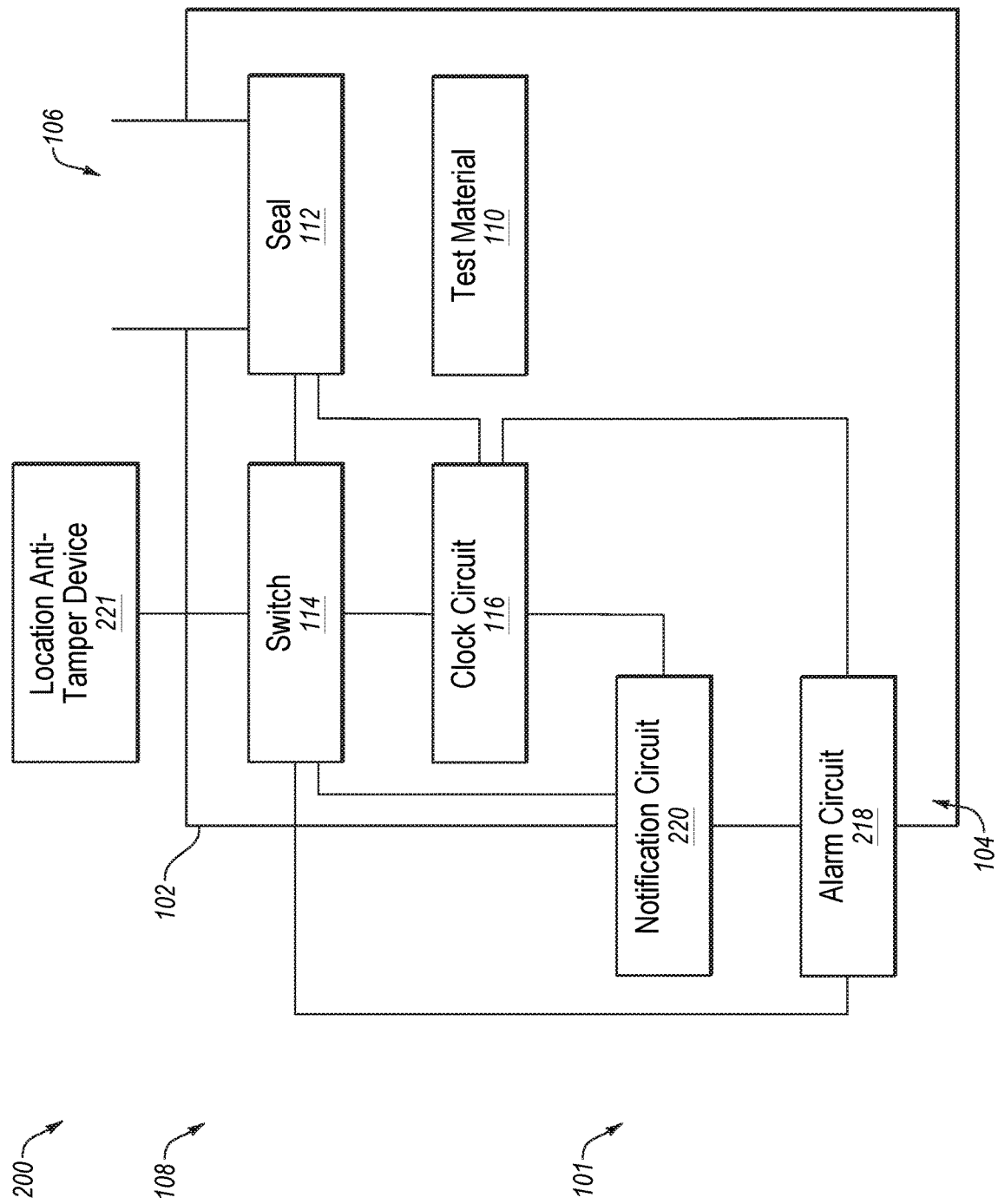
FIG. 2 illustrates a block diagram of another example radon detection device.

FIG. 2 illustrates a block diagram of another example radon detection device 200 (referred to in the present disclosure as "device 200"). The device 200 may also be configured to collect radon gas in the ambient air 108 to permit a lab to determine an Average Radon Level of the ambient air 108. The device 200 may also be configured to be in the sealed configuration or the open configuration to prevent the ambient air 108 from entering or to permit the ambient air 108 to enter the radon measurement device 104. FIG. 2 depicts the device 200 in the sealed configuration. The device 200 may also include a notification circuit 220 and an alarm circuit 218.

The notification circuit 220 may be communicatively coupled to the clock circuit 116. In some embodiments, the notification circuit 220 may also be communicatively coupled to the switch 114. The notification circuit 220 may be configured to provide one or more visual indicators, audible indicators, or both. The indicators may indicate to the user a current state or status of the radon test. For example, the indicators may indicate whether the radon test has not been started, is valid and in progress, or is complete.

In some embodiments, the notification circuit 220 may receive one or more messages from the clock circuit 116 including the time data. In some embodiments, the messages may indicate that the first timer is equal to zero, greater than zero but less than the measurement interval, or substantially equal to or greater than the measurement interval. Additionally, in some embodiments, the notification circuit 220 may determine whether the switch 114 is in the first position, the second position, or the lock position. The notification circuit 220 may determine whether the radon test has started, is valid and in progress, or is complete based on the messages received from the clock circuit 116, the position of the switch 114, or both.

In some embodiments, in response to the first timer being initiated and the switch 114 being in the lock position, the notification circuit 220 may provide a first visual indicator indicating that the radon test is in progress. Additionally, in some embodiments, in response to the first timer being substantially equal to or greater than the measurement interval and the switch 114 being in the first position, the notification circuit 220 may provide a second visual indicator indicating that the radon gas test is complete and that the second timer is going (e.g., the shipping time is currently being tracked).

Alternatively, in some embodiments, in response to the switch 114 transitioning from the first position to second position and concurrently to the lock position, the notification circuit 220 may provide the first visual indicator. Additionally, in these and other embodiments, in response to the switch 114 transitioning from the lock position to the first position, the notification circuit 220 may provide the second visual indicator.

The first visual indicator and the second visual indicator may include light emitted by one or more light sources (not illustrated). For example, the light sources may include one or more light emitting diodes (LEDs). In some embodiments, the first visual indicator and the second visual indicator may be provided by a single light source emitting different colors of light. For example, the first visual indicator may include green light emitted by a light source and the second visual indicator may include red light emitted by the same light source. In other embodiments, the first visual indicator and the second visual indicator may be provided by multiple light sources. For example, the first visual indicator may be provided by a first light source and the second visual indicator may be provided by a second light source. In some embodiments, the first visual indicator, the second visual indicator, or both may include light being emitted in a pattern (e.g., blinking) or light being emitted solidly by the light sources.

In some embodiments, the notification circuit 220 may provide a third visual indicator. The third visual indicator may indicate whether the switch 114 is in the second position. For example, when the switch 114 transitions from the first position to the second position, the third visual indicator may be provided by the light sources. In addition, when the switch 114 transitions to the lock position from the second position, the notification circuit 220 may stop providing the third visual indicator and may provide the first visual indicator, which may indicate that the radon test is valid and in progress. In some embodiments, the third visual indicator may be provided by a third light source. In other embodiments, the third visual indicator may be provided by the same light source as the first visual indicator, the second visual indicator, or both. Additionally, in some embodiments, the notification circuit 220 may include a visual readout (not illustrated) that provides the first visual indicator, the second visual indicator, the third visual indicator, or any combination thereof using plain language.

The alarm circuit 218 may be communicatively coupled to the clock circuit 116 and the switch 114. The alarm circuit 218 may be configured to provide an audible indicator (e.g. an audible alarm) or a visual alarm indicating that the switch 114 is in the second position for longer than an alarm period. In some embodiments, the alarm circuit 218 may receive one or more messages from the clock circuit 116 including the time data.

The alarm circuit 218 may compare the current value of the first timer to an alarm period. Responsive to the current value of the first timer being substantially equal to or greater than the alarm period, the alarm circuit 218 may be configured to determine whether the switch 114 is in the first position, the second position, or the lock position. Responsive to the current value of the first timer being substantially equal to or greater than the alarm period and the switch being in the second position, the alarm circuit 218 may provide the audible alarm (e.g., a first audible indicator), the visual alarm, or both The audible alarm and the visual alarm may indicate to the user that the radon test isn't fully initialized and the positioning of the switch 114 needs to be addressed.

The alarm circuit 218 may continue to determine whether the switch 114 is in the second position or the lock position. Responsive to the switch 114 transitioning to the lock position from the second position and the alarm circuit 218 providing the audible alarm or the visual alarm, the alarm circuit 218 may stop providing the audible alarm or the visual alarm. In some embodiments, the audible alarm may include a short harsh sound to cause the user to move the switch 114 to the lock position from the second position. In some embodiments, the visual alarm may include a light being emitted by a light source the same as or similar to the first visual indicator.

Additionally, the alarm circuit 218 may determine whether the first timer is substantially equal to or greater than the measurement interval. Responsive to the first timer being substantially equal to or greater than the measurement interval, the alarm circuit 218 may determine whether the switch 114 is in the first position. Responsive to the switch 114 being in the first position, the alarm circuit 218 may provide an additional audible alarm (e.g., a second audible indicator). The additional audible alarm may indicate to the user that the radon test is complete and that the device 200 should be sent to the lab to determine the Average Radon Level.

In some embodiments, the audible alarm and the additional audible alarm may include different sounds or any other appropriate audible alarms. For example, the additional audible alarm may include a harsh sound at relatively high decibels. In some embodiments, the decibels of the additional audible alarm may gradually increase as the value of the second timer increases. The increasing decibels of the additional audible alarm may increase the likelihood that the user notices that the radon test is complete and that the device 200 should be sent to the lab to calculate the Average Radon Level.

Additionally, for accurate radon measurement, the device 200 should be placed in a single physical location for the duration of the measurement interval. Physically moving the device 200 may undermine the accuracy of the radon test. For instance, if for half of the measurement interval, the device 200 is near a window and for the other half of the measurement interval, the device 200 is far from the window, then the difference in temperature, atmospheric conditions, etc. may impact the test material 110 and may change the collection of the radon gas by the test material 110.

Accordingly, in some embodiments, the device 200 may include a location anti-tamper device 221 (referred to in the present disclosure as "LATD 221"). The LATD 221 may be configured to detect when the device 200 is physically moved from an initial position in the environment 101. In a deployment configuration, the LATD 221 may be in a first position. In addition, when the device 200 is physically moved from the initial place in the environment 101, the LATD 221 may change to a second position. The position of the LATD 221 may be maintained in the first position by a feature or element of the structure. For example, the position of the LATD 221 may be maintained in the first position by a wall of the structure. Movement of the device 200 relative to the wall may cease maintenance of the LATD 221 in the first position.

In some embodiments, the LATD 221 may generate tamper data. The temper data may record when the device 200 was initially positioned in the environment 101 and when the device 200 has been physically moved from the initial position. Knowledge of if or when the device 200 was physically moved may indicate that the calculated Average Radon Level of the ambient air 108 may be accurate or inaccurate. For example, if the tamper data indicates that the device 200 was not moved prior to completion of the radon test, the Average Radon Level may be relatively accurate. As another example, if the tamper data indicates that the device 200 was moved prior to completion of the radon test, the Average Radon Level may be relatively inaccurate.

In some embodiments, the LATD 221 may be configured to determine whether the device 200 was physically moved from the initial position prior to the switch 114 transitioning to the first position from the lock position. For example, the tamper data may include a date and time stamp indicating when the device 200 is physically moved from the initial position and the second timer may include a date and time stamp indicating when the second timer started. In some embodiments, the LATD 221 may compare the date and time stamp in the tamper data to the date and time stamp of when the second timer started to determine whether the device 200 was moved prior to the radon test being completed. Alternatively, a technician at the lab or the user may compare the date and time stamp in the tamper data to the date and time stamp of when the second timer started to determine whether the device 200 was moved prior to the radon test being completed.

In some embodiments, the LATD 221 may include a tab (not illustrated) and a release button (not illustrated). In these and other embodiments, the tab may be removed from the LATD 221 and a portion of the release button may extend away from the housing 102 (e.g., the release button may change to the first position). Additionally, depressing the release button may cause the release button to be in the second position. For example, the device 200 may include adhesive that adheres the device 200 to the surface of the structure. Adhering the device 200 to the surface may depress the release button and may maintain the release button in the second position. The release button being depressed may indicate that the device 200 has been placed in the initial position. In some embodiments, the tamper data may include a first date and time stamp indicating when the release button was first placed in the second state (e.g., when the device 200 was initially placed in the environment 101) and a second date and time stamp when the button was placed in the second state (e.g., when the device 200 was physically moved from the initial position).

In some embodiments, the LATD 221 may include a light sensor (not illustrated) and a light source (not illustrated). When the device 200 is positioned in the initial position, the light source may emit light toward the surface of the structure. Additionally, when the device 200 is positioned in the initial position, the LATD 221 may generate the first date and time stamp. The light sensor may detect light reflecting off of the surface of the structure. Responsive to the amount of light being detected by the light sensor changing more than a threshold value, the LATD 221 may generate the second date and time stamp indicating when the light changed (e.g., when the device 200 was physically moved from the initial position).

In these and other embodiments, the LATD 221 may determine whether a difference between the first date and time stamp and the second date and time stamp is substantially equal to or greater than the measurement interval. Responsive to the difference between the first date and time stamp and the second date and time stamp being substantially equal to or greater than the measurement interval, the tamper data may indicate that the device 200 was not moved during the radon test. Alternatively, responsive to the difference between the first date and time stamp and the second date and time stamp being substantially less than the measurement interval, the tamper data may indicate that the device 200 was moved during the radon test.

In some embodiments, the LATD 221 may include a pad (not illustrated) that can separate when the device 200 is physically moved from the initial position. In these and other embodiments, a first portion of the pad may include the adhesive for mounting the device 200 on the surface of the structure. When the device 200 is physically moved from the initial position, the first portion of the pad may separate from the pad and remain adhered to the surface of the structure. Additionally, a second portion of the pad may remain attached to the device 200. The first portion of the pad may be removable from the surface of the structure to be disposed of.

Modifications, additions, or omissions may be made to the device 200 without departing from the scope of the present disclosure. The present disclosure applies to the device 200 including various combinations of components (e.g., 110, 112, 114, 116, 218, 220, 221, etc.) and different numbers of such components. Moreover, the separation of various components in the embodiments described in the present disclosure is not meant to indicate that the separation occurs in all embodiments. Moreover, it may be understood with the benefit of this disclosure that the described components may be integrated together in a single component or separated into multiple components.

Figure 3:
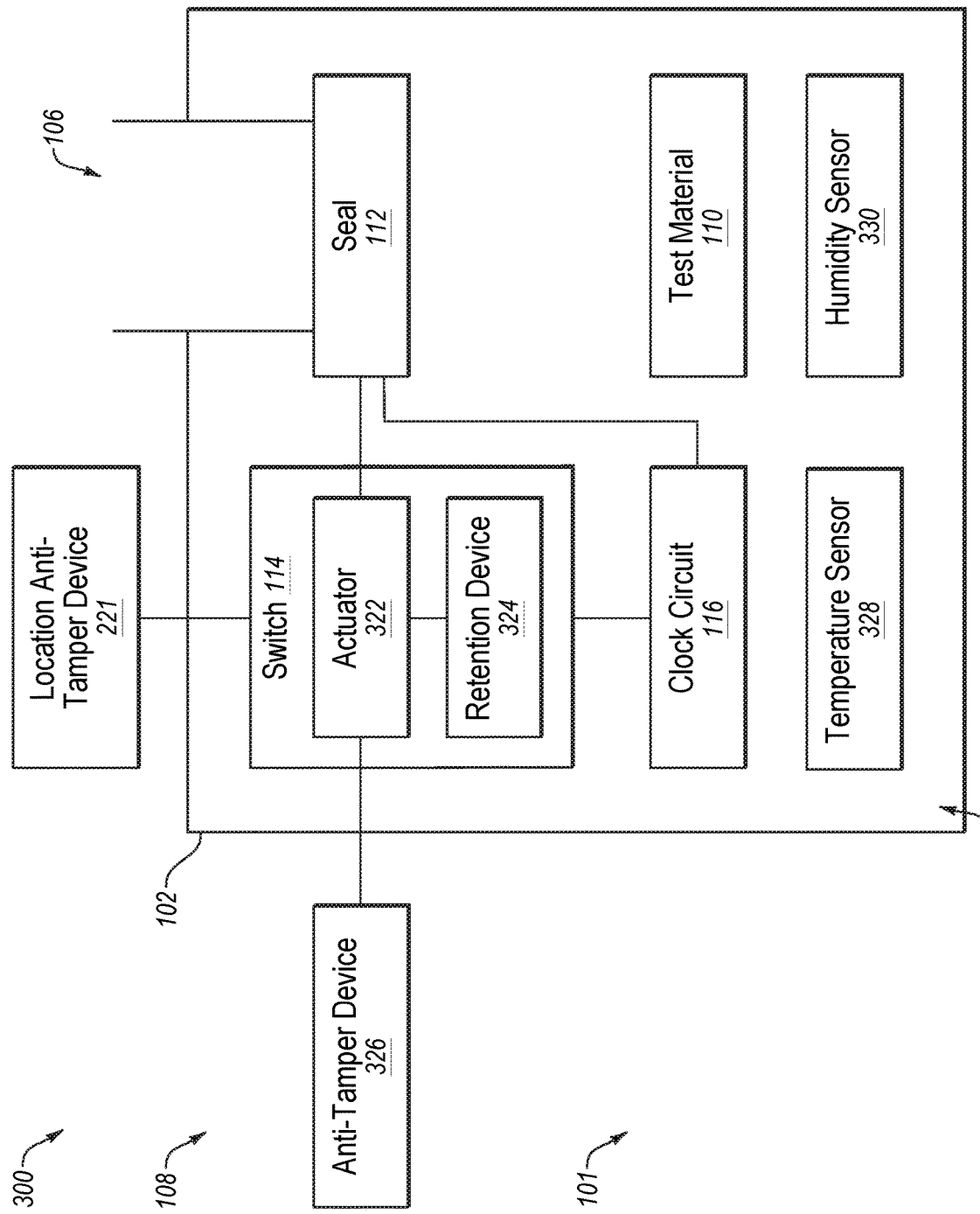
FIG. 3 illustrates a block diagram of yet another example radon detection device.

FIG. 3 illustrates a block diagram of yet another example radon detection device 300 (referred to in the present disclosure as "device 300"). The device 300 may also be configured to collect radon gas in the ambient air 108 to permit a lab to determine an Average Radon Level of the ambient air 108. The device 300 may also be configured to be in the sealed configuration or the open configuration to prevent the ambient air 108 from entering or to permit the ambient air 108 to enter the radon measurement device 104. FIG. 3 depicts the device 300 in the sealed configuration.

In some embodiments, the switch 114 may include an actuator 322 and a retention device 324. The actuator 322 may be configured to cause the seal 112 to transition between the open position and the seal position. For example, the actuator 322 may transition between the first position, the second position, and the lock position. Additionally, the retention device 324 may be configured to prevent the actuator 322 from transitioning from the lock position to the first position prior to the first timer being substantially equal to the measurement interval. Likewise, the retention device 324 may be configured to automatically cause the actuator 322 to transition to the first position so that the seal 112 transitions to the seal position from the open position when the first timer is substantially equal to the measurement interval.

In some embodiments, the actuator 322 may include one or more of a push button, a pull lever, a turn dial, a diaphragm, an aperture, and an electrical switch to cause the seal 112 to transition between the open position and the seal position. In these and other embodiments, the retention device 324 may include one or more of a slider and an aperture.

In some embodiments, the switch 114 may include one or more portions that are configured to physically move independent of or relative to each other. In these and other embodiments, a first portion of the switch 114 may form a portion of the housing 102 and the triggering actions may include rotation of one or more portions of the housing 102. In some embodiments, a first portion of the switch 114 may be disposed within the radon measurement device 104 and a second portion of the switch 114 may be positioned external to the radon measurement device 104. In other embodiments, the entire switch 114 may be positioned external to the radon measurement device 104

The device 300 may also include additional components, which may include an anti-temper device 326 (referred to in the present disclosure as "ATD 326"), a temperature sensor 328, and a humidity sensor 330. The ATD 326 may be communicatively coupled to the actuator 322. The ATD 326 may determine whether the actuator 322 was caused to transition from the lock position to the first position by means other than the retention device 324. For example, the ATD 326 may determine whether the retention device 324 applied a force on the actuator 322 or if an external item (e.g., a human being) applied a force on the actuator 322.

The temperature sensor 328 and the humidity sensor 330 may be disposed in the radon measurement device 104. The temperature sensor 328 may be configured to determine and track a temperature the ambient air 108 introduced into the radon measurement device 104 during the measurement interval. In some embodiments, the temperature sensor 328 may determine and track an average, a high, a low, or all three temperature points of the ambient air 108 during the measurement interval. In other embodiments, the temperature sensor 328 may determine and track a continuous temperature of the ambient air 108 during the measurement interval.

The humidity sensor 330 may be configured to determine and track a humidity level of the ambient air 108 introduced into the radon measurement device 104 during the measurement interval. In some embodiments, the humidity sensor 330 may determine and track an average, a high, a low, or all three humidity level points of the ambient air 108 during the measurement interval. In other embodiments, the humidity sensor 330 may determine and track a continuous humidity level of the ambient air 108 during the measurement interval.

The radon detection device 300 is depicted with the humidity sensor 330 and the temperature sensor 328. In other embodiments, the radon detection device 300 may include one or more other sensors. The one or more other sensors may be configured to measure environmental conditions present during an acquisition phase of the device 300. Some additional sensors may include an accelerometer, a barometer, a light sensor, gas concentration sensor, air velocity sensor, and the like.

Modifications, additions, or omissions may be made to the device 300 without departing from the scope of the present disclosure. The present disclosure applies to the device 300 that has various combinations of components (e.g., 110, 112, 114, 116, 218, 220, 221, 322, 324, 326, 328, 330, etc.) and different numbers of such components. Moreover, the separation of various components in the embodiments described in the present disclosure is not meant to indicate that the separation occurs in all embodiments. Moreover, it may be understood with the benefit of this disclosure that the described components may be integrated together in a single component or separated into multiple components.

For example, in these and other embodiments, the seal 112 may include any structure or any materials suitable for discouraging fluid communication between the test material 110 and the ambient air 108. In some embodiments, the seal 112 may include a cap that fits over an opening of the vent 106. For instance, the seal 112 may include a threaded cap that mechanically engages counterpart threads on an opening of the vent 106. In some configurations, the seal 112 may include an elastic cap, such as a rubber cap, sized and shaped to fit over an opening of the vent. In some forms, the seal 112 may include a rigid cap.

In these and other embodiments, the seal 112 may include a gasket such as a washer, an O-ring, pre-cured silicone or other gel, or the like to encourage a fluid-tight interface between the seal 112 and the vent 106. In some configurations, the seal 112 or the vent 106 may include a magnet and the other of the seal or the vent 106 may include a second magnet or magnetic material positioned such that the seal 112 may be held in place relative to the vent 106.

Alternately or additionally, the seal 112 may include a plug that fits at least partially within the vent 106. For instance, the seal 112 may include an elastomer plug, such as a rubber stopper; a pliable plug, such as a cork stopper or a wax plug; a threaded plug that mechanically engages counterpart threads in the opening of the vent 106; or the like.

In some configurations, the seal may alternately or additionally include a fluid valve. For example, the seal 112 may include a ball valve, a solenoid valve, a plug valve, a butterfly valve, a membrane or diaphragm valve, a gate valve, a globe valve, a pinch valve, a cam-driven valve, or other fluid valve suitable for discouraging fluid communication between the test material 110 and the ambient air 108.

Alternately or additionally, the seal 112 may include a trap door style or gate style sealing mechanism. For instance, the seal 112 may include a structure configured to rotates, slide, or otherwise move into a position on or in the vent 106 in a manner that discourages fluid communication between the ambient air 108 and the test material 110. By way of example, the seal 112 may include a disk-shaped structure that defines an opening in part of the disk. When the opening is aligned with the vent 106, the test material 110 may be in fluid communication with the ambient air 108. When the opening is not aligned with the vent 106, the disk may discourage fluid communication between the test material 110 and the ambient air 108.

In these and other embodiments, the seal 112 may include two sealing devices. For instance, a first sealing device of the seal 112 may include a polymer film or the like located across an opening of the vent. The seal 112 may, for instance, transition from a sealed position to an open position by puncturing, cutting, melting, removing, dissolving, or otherwise transforming the first sealing device of the seal 112 such that the test material is in fluid communication with the ambient air 108. Alternatively, a different first sealing device may be used. The seal 112 may transition from the open position to the sealed position by moving the second sealing device of the seal 112 to the vent 106 such that fluid communication is discouraged between the test material 110 and the ambient air 108. By way of example, the second sealing device of the seal 112 may include a cap, a plug, a trapdoor, a gate, a fluid valve, a magnet, or the like. In some configurations, employing two sealing device as the seal 112 may facilitate a seal 112 that may be closed in a different manner than the seal 112 is opened, which may encourage relatively secure sealing of the vent 106 before the seal 112 is opened and after the seal 112 is closed. For instance, the use of two sealing devices to form the seal 112 may efficiently discourage the test material 110 from being exposed to the ambient air 108 prior to the first triggering action or after the third triggering action.

Regarding the actuator 322, these and other embodiments may employ actuator configurations and actuation methods suitable for moving the corresponding seal 112 from the seal position to the open position or from the open position to the seal position. By way of example, a spring-loaded or elastic-loaded actuator 322 may be used. For instance, a helical-coil spring, such as a tension spring, a compression spring, or a torsion spring may be used. Alternately or additionally, a leaf or beam spring, or rubber spring may be used.

Alternately or additionally, the actuator 322 may include a motor. For instance, the actuator 322 may include a DC electric motor, a servo motor, a stepper motor, or the like. In some configurations, the motor may drive a worm gear, a spur gear, a cam, or the like that interfaces with the seal 112 or a latch that releases the seal 112 to be moved by a spring-loaded or elastic-loaded portion of the actuator 322. In some embodiments, the seal 112 may be attached directly to a shaft of the motor such that the motor may move the seal 112 from the seal position to the open position or from the open position to the seal position directly. Alternately or additionally, the actuator 322 may include a solenoid actuator that interfaces with the seal 112 or a latch that releases the seal 112.

In some configurations, the actuator 322 may include a latch configured to maintain the seal 112 in the seal position or the open position until such time that the seal is to transition to the seal position from the open position or to the open position from the seal position. In response to the latch releasing the seal 112, spring loading applied to the seal 112 may encourage the seal 112 to move from the seal position to the open position or from the open position to the seal position. In some configurations, two latches and two spring-loading devices may be employed such that a first latch and a first spring-loading device encourages the seal 112 to transition from the seal position to the open position and a second latch and a second spring-loading device encourages the seal 112 to transition from the open position to the seal position.

By way of example, the latch may include a mechanical latch, such as hinged catch that restrains the spring-loaded seal 112 and is disengaged by way of a motor or solenoid actuator such that the spring loading encourages the seal 112 to move. Alternately or additionally, the latch may include a solenoid actuator that employs an extended plunger of the solenoid to act as the latch and releases the latch by retracting the plunger.

In an example configuration, a radon detection device generally corresponding to the device 300 of FIG. 3 may include a motor actuator 322. The motor may be configured to drive a lead screw, also described as a power screw. The lead screw may interface with counterpart threads on a plug-style seal 112. In some configurations, the seal 112 may be movably positioned on guides to encourage the seal 112 to follow a desired path when the motor actuator 322 runs. Running the motor in a first direction may cause the plug-style seal 112 to move out of the vent 106 such that the seal 112 transitions from the seal position to the open position. Running the motor in a second direction opposite to the first direction may cause the plug-style seal 112 to move into the vent 106 such that the seal 112 transitions from the open position to the seal position.

In another example configuration, another radon detection device generally corresponding to the device 300 of FIG. 3 may include a motor actuator 322 attached to a threaded, cylindrical, plug-style seal 112. Counterpart threads may be formed on an interior of a tubular, correspondingly sized vent 106. Running the motor in a first direction may cause the threaded seal 112 to rotate and move out of the threaded vent 106 such that the seal 112 transitions from the seal position to the open position. Running the motor in a second direction opposite to the first direction may cause the threaded seal 112 to engage the threaded vent 106 such that the seal 112 transitions from the open position to the seal position.

In still another example configuration, still another radon detection device generally corresponding to the device 300 of FIG. 3 may include a motor actuator 322 attached to a threaded, cylindrical, cap-style seal 112. Counterpart threads may be formed on an exterior of a tubular, correspondingly sized vent 106. Running the motor in a first direction may cause the threaded seal 112 to rotate and move off of the threaded vent 106 such that the seal 112 transitions from the seal position to the open position. Running the motor in a second direction opposite to the first direction may cause the threaded seal 112 to engage the threaded vent 106 such that the seal 112 transitions from the open position to the seal position.

In yet another example configuration, yet another radon detection device generally corresponding to the device 300 of FIG. 3 may include a motorized aperture-style seal 112. The seal 112 may include multiple blades or leaves that are each configured to be rotated in-plane. The blades may be rotated to move the blades from positions that obstruct the vent 106 to positions that do not obstruct the vent such that the seal 112 transitions from the seal position to the open position. The blades may further be rotated to move the blades from the positions that do not obstruct the vent 106 to the positions that do obstruct the vent such that the seal 112 transitions from the open position to the seal position.

In a further example configuration, a further radon detection device generally corresponding to the device 300 of FIG. 3 may include a solenoid actuator 322. A plunger of the solenoid may be attached to a plug-style seal 112. The plunger of the solenoid may be retracted to cause the seal 112 to move out of the vent 106 such that the seal 112 transitions from the seal position to the open position. Extending the plunger of the solenoid may cause the seal 112 to move into the vent 106 such that the seal 112 transitions from the open position to the seal position.

An example radon detection device generally corresponding to the device 300 of FIG. 3 may include a plug-style seal 112 spring-loaded such that a force exerted by the spring encourages the seal 112 towards the vent 106. A catch may restrain the seal 112 until a triggering mechanism, such as a plunger of a solenoid actuator 322, moves the catch and causes the catch to disengage from the seal 112. In response to the catch being disengaged, the spring loading may cause the seal 112 to enter the vent 106 such that the seal 112 transitions from the open position to the seal position.

Another example radon detection device generally corresponding to the device 300 of FIG. 3 may include a trap door-style seal 112 spring-loaded such that a force exerted by the spring encourages the seal 112 towards the vent 106. A catch may restrain the seal 112 until a triggering mechanism, such as a plunger of a solenoid actuator 322, moves the catch and causes the catch to disengage from the seal 112. In response to the catch being disengaged, the spring loading may cause the seal 112 to cover the vent 106 such that the seal 112 transitions from the open position to the seal position.

Still another example radon detection device generally corresponding to the device 300 of FIG. 3 may include a threaded, cylindrical, plug-style seal 112 spring-loaded such that a force exerted by the spring encourages the seal 112 towards a tubular vent 106 having counterpart threads formed on its interior and encourages the seal 112 to rotate. For example, the seal 112 may engage with a combination of a helical compression and torsion spring, described herein as a directional spring. A catch may restrain the seal 112 until a triggering mechanism, such as a plunger of a solenoid actuator 322, moves the catch and causes the catch to disengage from the seal 112. In response to the catch being disengaged, the spring loading may cause the seal 112 to both rotate and to move to engage with the counterpart threading in the vent 106 such that the seal 112 transitions from the open position to the seal position.

Yet another example radon detection device generally corresponding to the device 300 of FIG. 3 may include a threaded cap-style seal 112 spring-loaded such that a force exerted by the spring encourages the seal 112 towards a tubular vent 106 having counterpart threads formed on its exterior and encourages the seal to rotate. For example, the seal 112 may engage with a directional spring. A catch may restrain the seal 112 until a triggering mechanism, such as a plunger of a solenoid actuator 322, moves the catch and causes the catch to disengage from the seal 112. In response to the catch being disengaged, the spring loading may cause the seal 112 to both rotate and to move to engage with counterpart threading on the vent 106 such that the seal 112 transitions from the open position to the seal position.

A further example radon detection device generally corresponding to the device 300 of FIG. 3 may include a disk-shaped seal 112 having an opening formed therein. The opening of the seal 112 may be positioned such that the seal 112 does not obstruct the vent 106. The disk-shaped seal 112 may be spring-loaded to encourage the seal 112 to rotate. A catch may restrain the seal 112 until a triggering mechanism, such as a plunger of a solenoid actuator 322, moves the catch and causes the catch to disengage from the seal 112. In response to the catch being disengaged, the spring loading may cause the seal 112 to rotate such that the opening is moved away from the vent and a solid portion of the disk-shaped seal 112 obstructs the vent such that the seal 112 transitions from the open position to the seal position.

In some embodiments, the seal 112 may include pliable materials in the shape of a tube and in fluid communication with the vent 106. For example, the seal 112 may include a tubular length of an elastomer such as silicone. The seal 112 may be spring loaded such that the seal 112 is encouraged to rotate about an axis of the seal 112. A catch may restrain the seal 112 until a triggering mechanism, such as a plunger of a solenoid actuator 322, moves the catch and causes the catch to disengage from the seal 112. In response to the catch being disengaged, the spring loading may cause the seal 112 to rotate such that the pliable material twists shut such that the seal 112 transitions from the open position to the seal position. Alternately, the pliable seal 112 may be rotated by a motor actuator 322 or the like.

In some configurations, the seal 112 may include a flexible polymer having a zip lock, also described as a press-to-seal zipper, a press-and-seal zipper, or a slider-style zipper. A slider configured to press the zip lock closed may be traversed across the zip lock via the actuator 322. By way of example, the slider may be driven by a lead screw attached to a motor actuator 322 such that the slider slides across the length of the zip lock. Alternately or additionally, the polymer film may include an adhesive that adheres the polymer to itself or to an adjacent surface. The portion of the polymer seal 112 on which the adhesive is applied may be pressed against the counterpart surface by way of a slider, a cam, a spring-loaded pressing device, or the like. Alternately or additionally, the polymer seal 112 may be rolled up or folded up to transition to the seal position. For instance, the flexible polymer seal 112 may be attached to a shaft driven by a motor actuator 322, which may encourage the polymer seal 112 to roll up or fold up to transition to the seal position.

Figure 4A:
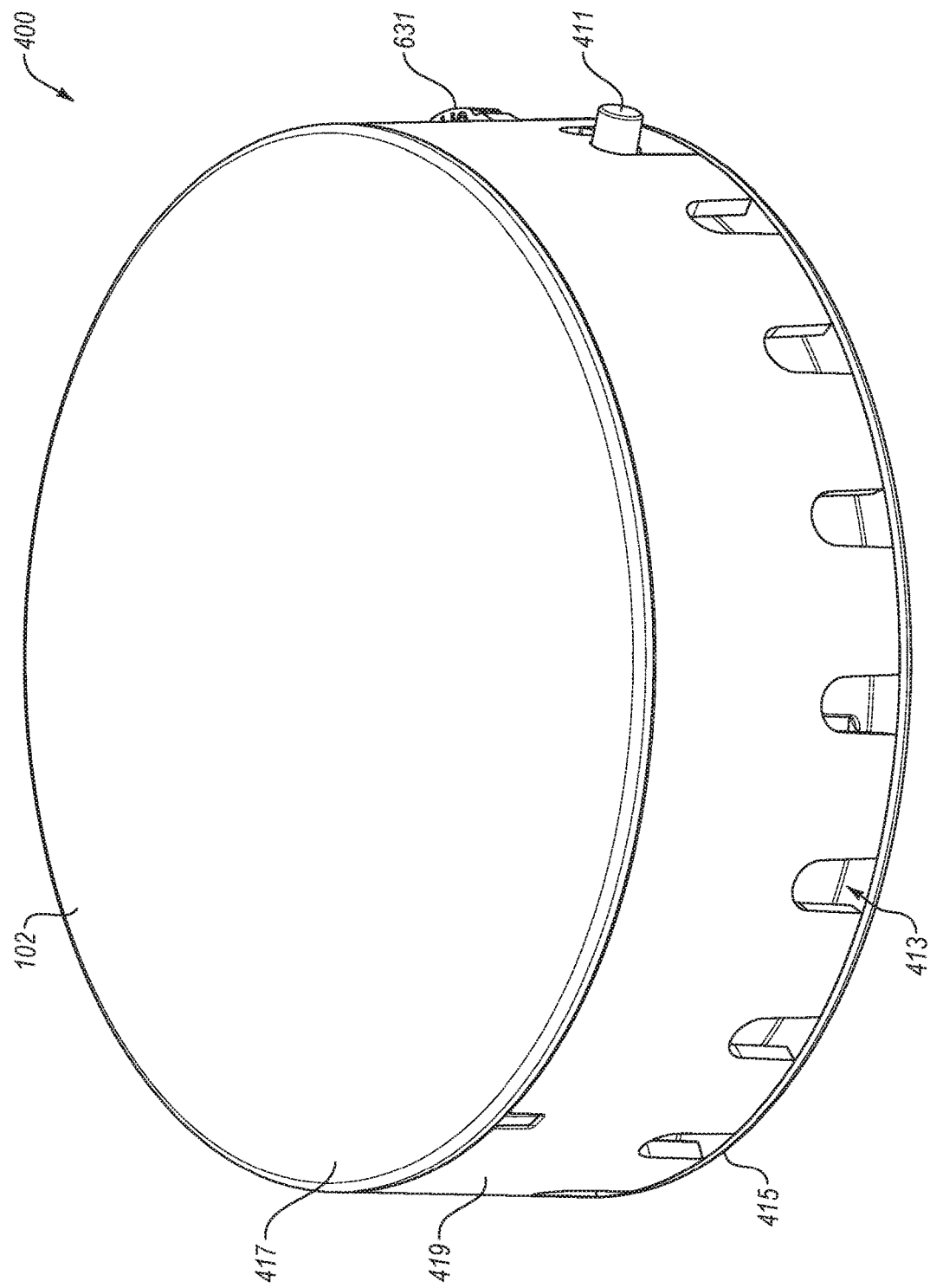
FIG. 4A illustrates a top perspective view of an example radon detection device.
Figure 4C:
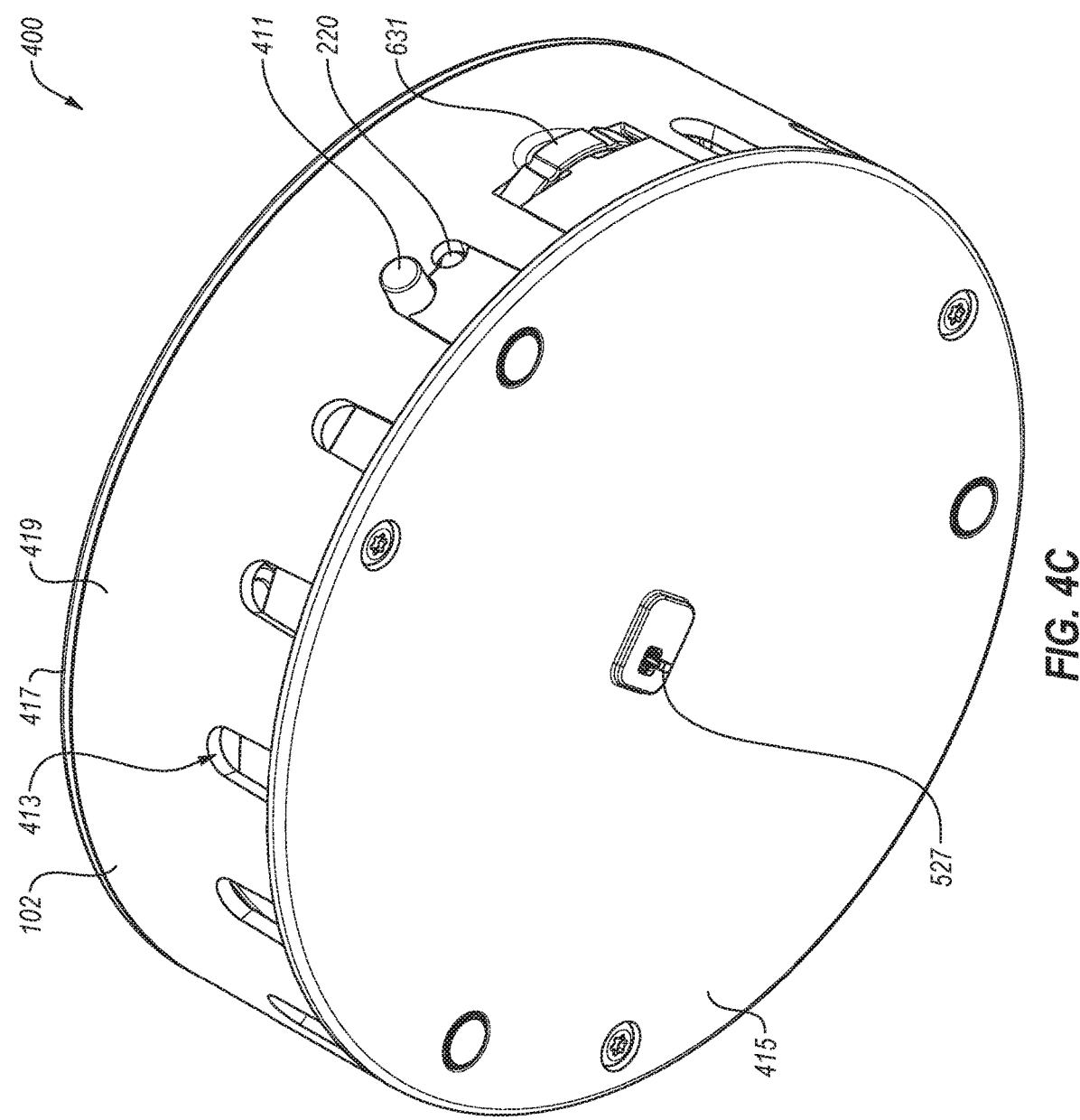
FIG. 4C illustrates a bottom perspective of the example radon detection device.

FIG. 4A illustrates a top perspective view of an example radon detection device 400. FIG. 4B illustrates a side view of the example radon detection device 400. FIG. 4C illustrates a bottom perspective of the example radon detection device 400.

With combined reference to FIGS. 4A-4C, the radon detection device 400 may include a top plate 417, a bottom plate 415, and a sidewall portion 419. The top plate 417, the bottom plate 415, and the sidewall portion 419 may form the housing 102 of the radon detection device 400. The sidewall portion 419 may define multiple environmental openings 413. A single environmental opening 413 is numbered in the Figures for ease of discussion. The environmental openings 413 may fluidly couple a chamber 1250 (illustrated in FIGS. 11A and 11B) of the radon detection device 400 to an external environment.

In addition, the radon detection device 400 may include an activation switch 411. In some embodiments, the activation switch 411 may be the same as or similar to the switch 114 discussed above in relation FIGS. 1-3. The activation switch 411 may be used to initiate exposure of test material 1041 (illustrated in FIG. 9B) to the external environment. The radon detection device 400 may also include an anti-tamper switch 527 positioned on or near the bottom plate 415. In some embodiments, the anti-tamper switch 527 may be the same as or similar to the location anti-tamper device 221 discussed above in relation to FIGS. 2 and 3. The anti-tamper switch 527 may be used to determine if the radon detection device 400 was physically moved while the radon detection device 400 is in the open configuration.

The radon detection device 400 may include a timer dial 631. The timer dial 631 may be configured to program an amount of time the test material 1041 is to be exposed to the external environment. In addition, the notification circuit 220 may indicate whether the radon detection device 400 is in the sealed or open configuration as discussed above in relation to FIGS. 2 and 3. The radon detection device 400 may be configured to communicatively couple to an external cable 423. The external cable 423 may be communicatively coupled to electronic components within the radon detection device 400 to obtain data stored in a memory (not illustrated).

In the embodiment of FIGS. 4A-4C, the external cable 423 may enable information and data to be accessed from the device 400. In other embodiments, the device 400 may include another type of communication unit, which may be configured to enable access to or to communicate information and data via a wireless network. For example, the communication unit may include one or more pieces of hardware configured to receive and send communications. In some embodiments, the communication unit may include one or more of an antenna, a wired port, and modulation/demodulation hardware, among other communication hardware devices. In particular, the communication unit may be configured to receive a communication from outside the device and to present the communication to a processor or to send a communication from the device 400 or a processor therein to another device or network. In some embodiments, the network includes or is configured to include a BLUETOOTH® communication network, a Wi-Fi communication network, a ZigBee communication network, an extensible messaging and presence protocol (XMPP) communication network, a cellular communications network, any similar communication networks, or any combination thereof for sending and receiving data.

Moreover, in some embodiments, the device 400 may include a communication unit configured for interface with a particular piece of laboratory equipment that accesses information related to radon exposure.

The external cable 423 may provide power to the device 400. For instance, the external cable 423 may be plugged into a power source. In other embodiments, the device 400 may include a battery or a battery pack. In these embodiments, the device 400 may not include the external cable 423 during operation (e.g., radon detection) by a user. Additionally, in these and other embodiments, the external cable 423 may allow for charging of the device 400.

Figure 5A:
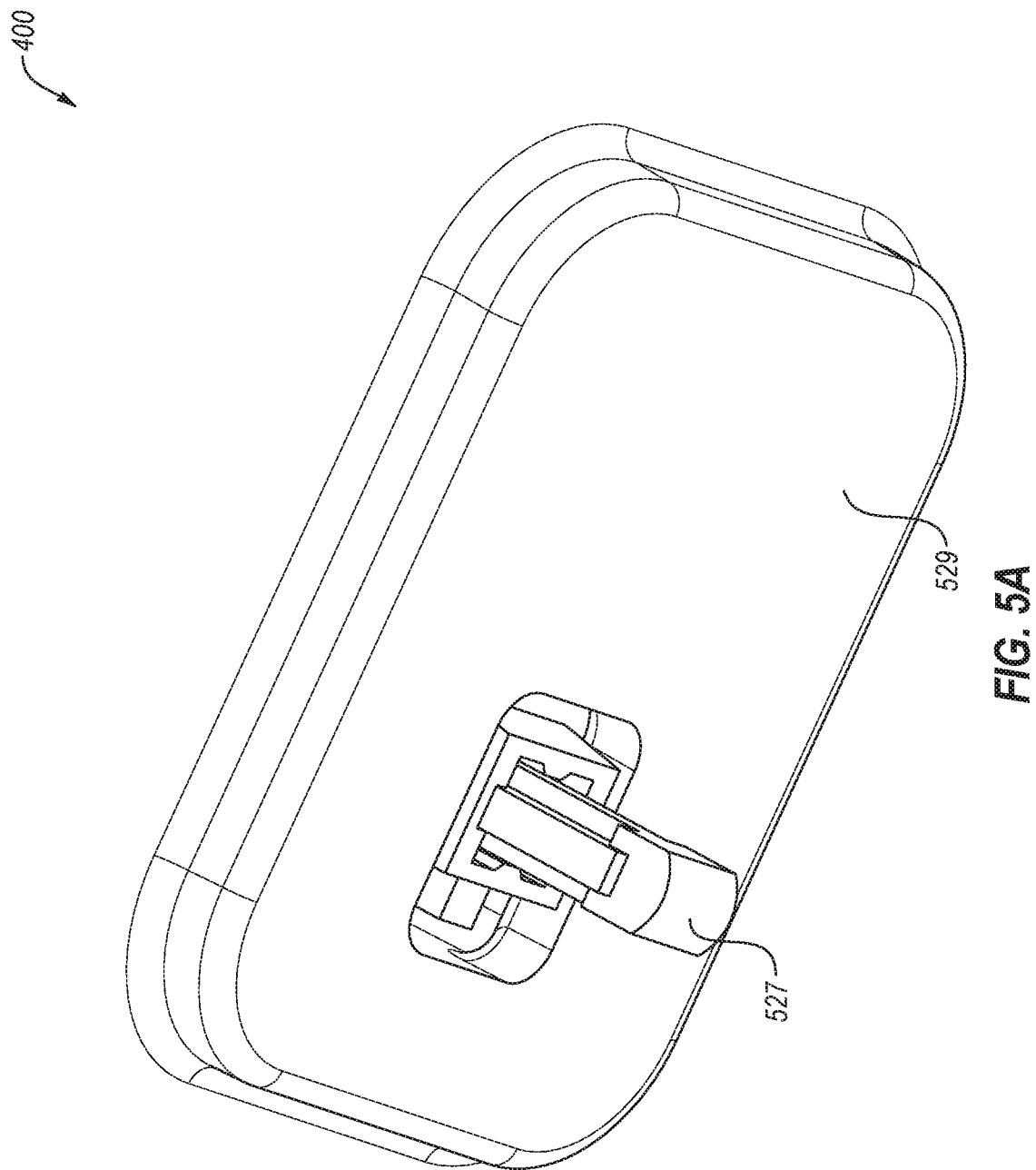
FIG. 5A illustrates a perspective view of an example anti-tamper switch including a housing plate that may be implemented in the radon detection device of FIGS. 4A-4C.
Figure 5B:
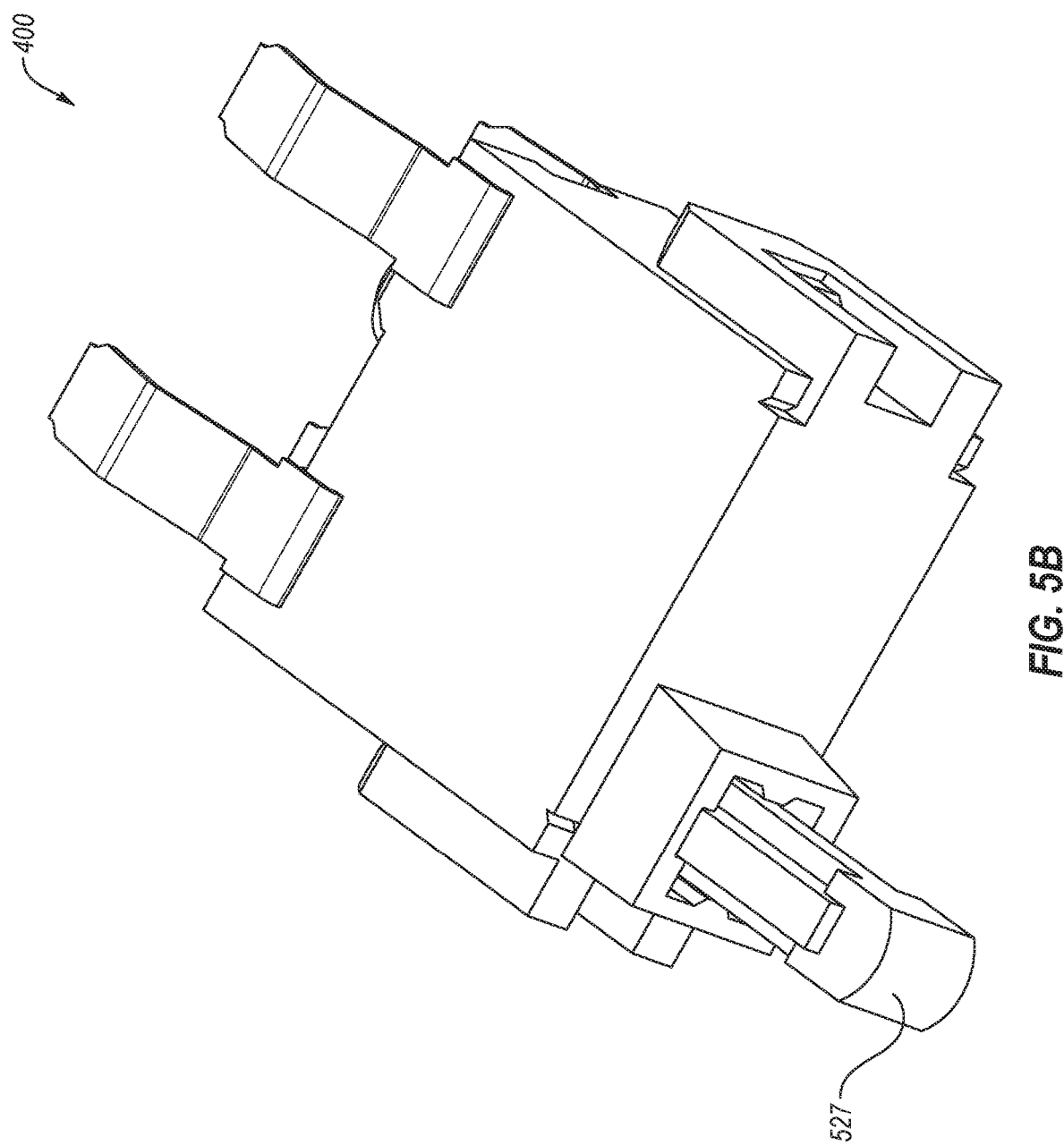
FIG. 5B illustrates a perspective view of the example anti-tamper switch of FIG. 5A.
Figure 5C:
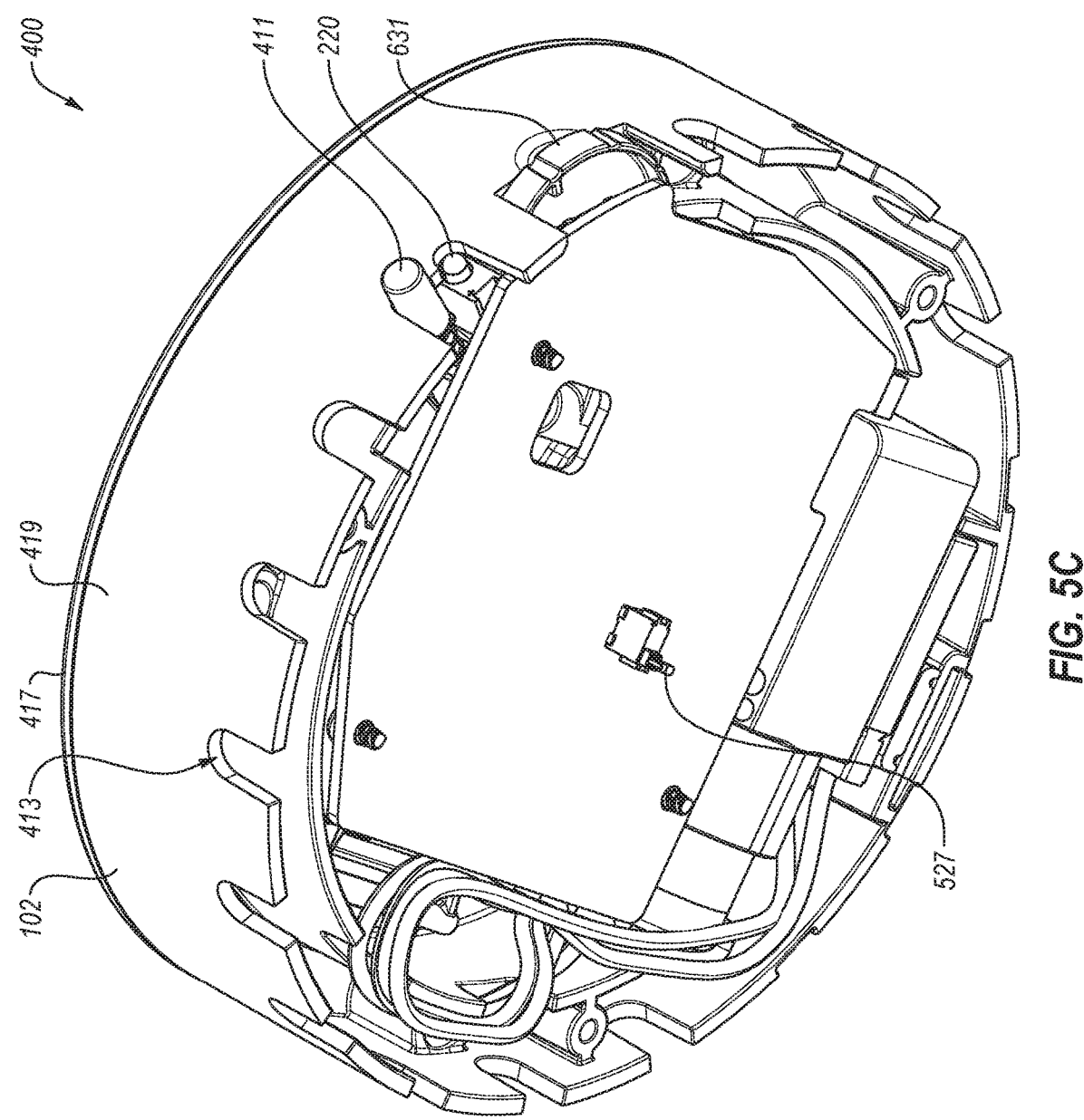
FIG. 5C illustrates a bottom perspective view of the radon detection device of FIGS. 4A-4C with a bottom plate removed to illustrate internal components of the anti-tamper switch.

FIG. 5A illustrates a perspective view of the example anti-tamper switch 527 including a housing plate 529 that may be implemented in the radon detection device 400 of FIGS. 4A-4C. FIG. 5B illustrates a perspective view of the example anti-tamper switch 527 of FIG. 5A. FIG. 5C illustrates a bottom perspective view of the radon detection device 400 of FIGS. 4A-4C with the bottom plate 415 removed to illustrate internal components of the anti-tamper switch 527. With combined reference to FIGS. 5A-5C, a portion of the anti-tamper switch 527 may extend beyond the housing plate 529. In some embodiments, the anti-tamper switch 527 may include a pressure switch. In these and other embodiments, when the radon detection device 400 is placed in the external environment, the anti-tamper switch 527 may be depressed. Electrical components of the radon detection device 400 may monitor an amount of time between the anti-tamper switch 527 being depressed and the anti-tamper switch 527 extending to determine an amount of time the radon detection device 400 was in the initial position in the external environment.

Figure 6:
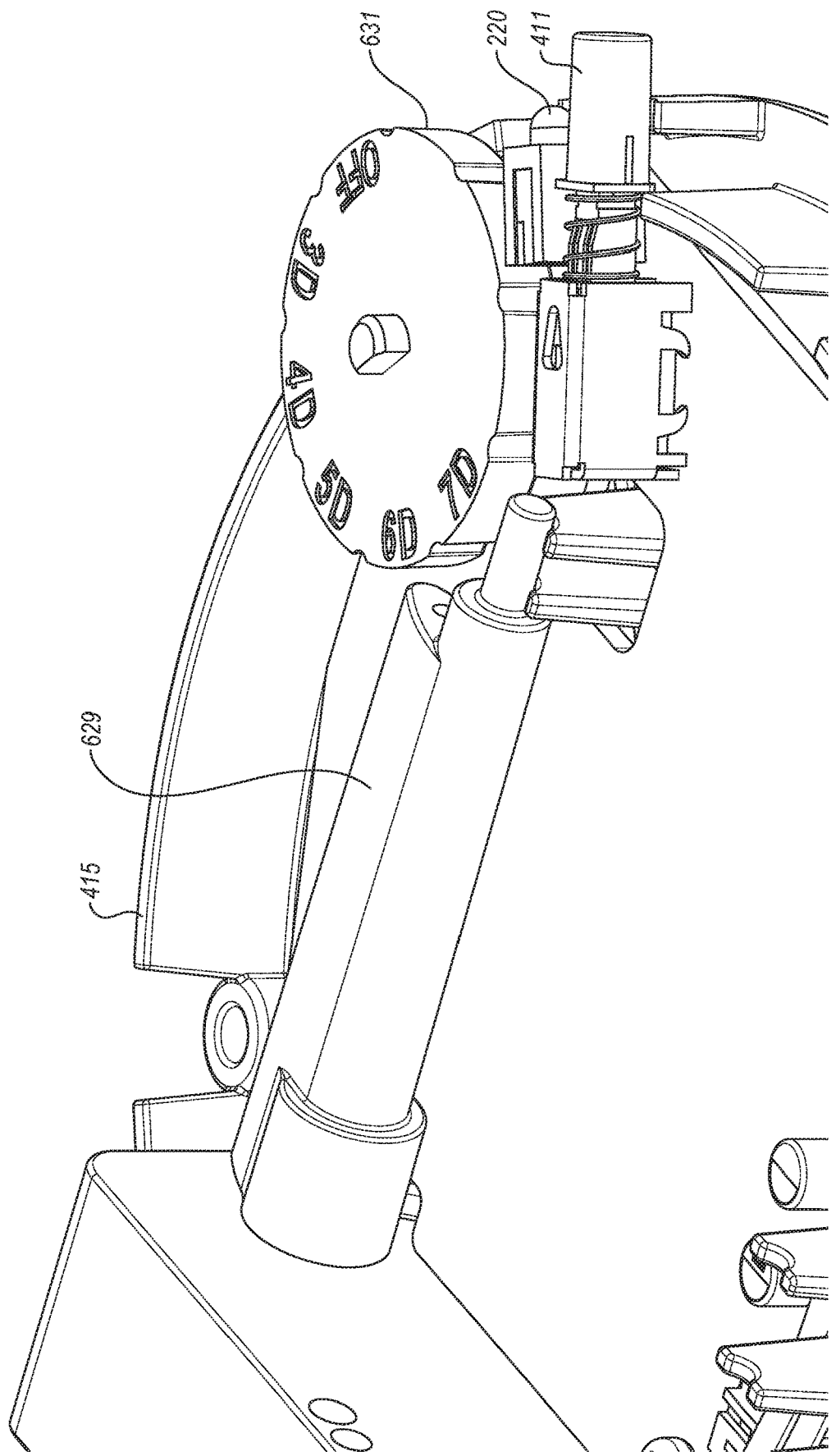
FIG. 6 illustrates a sectional view of the radon detection device of FIGS. 4A-4C with multiple pieces removed to illustrate internal components of the radon detection device.

FIG. 6 illustrates a sectional view of the radon detection device 400 of FIGS. 4A-4C with multiple pieces removed to illustrate internal components of the radon detection device 400. The radon detection device 400 may include a camshaft 629. The camshaft 629 may be positionable in an open position or in a seal position. In the seal position, the chamber 1251 may be hermetically sealed, which may prevent the test material 1041 from being exposed to the ambient air in the external environment. In the open position, the chamber 1251 may be exposed to the ambient air in the external environment.

Figure 7A:
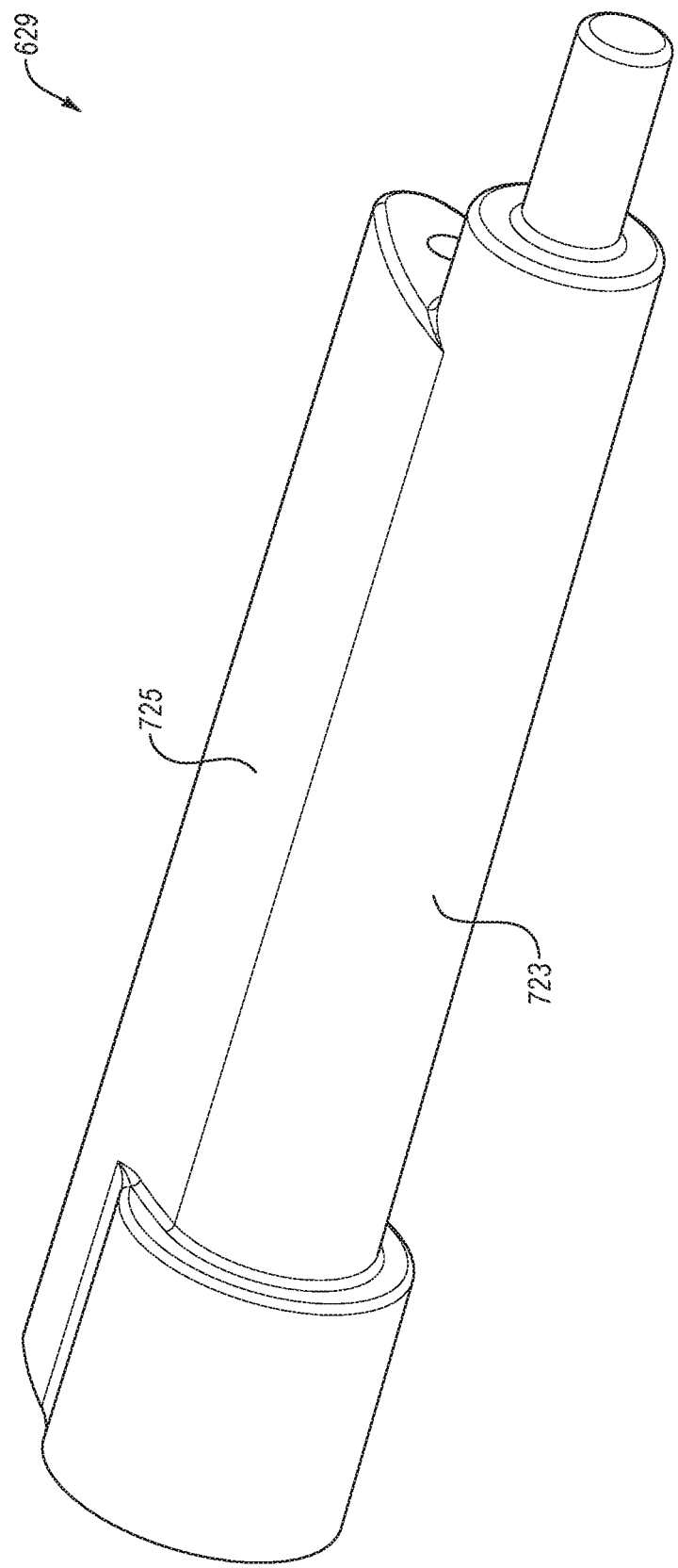
FIG. 7A illustrates a bottom perspective view of a cam shaft that may be implemented in the radon detection device of FIGS. 4A-4C.
Figure 7B:
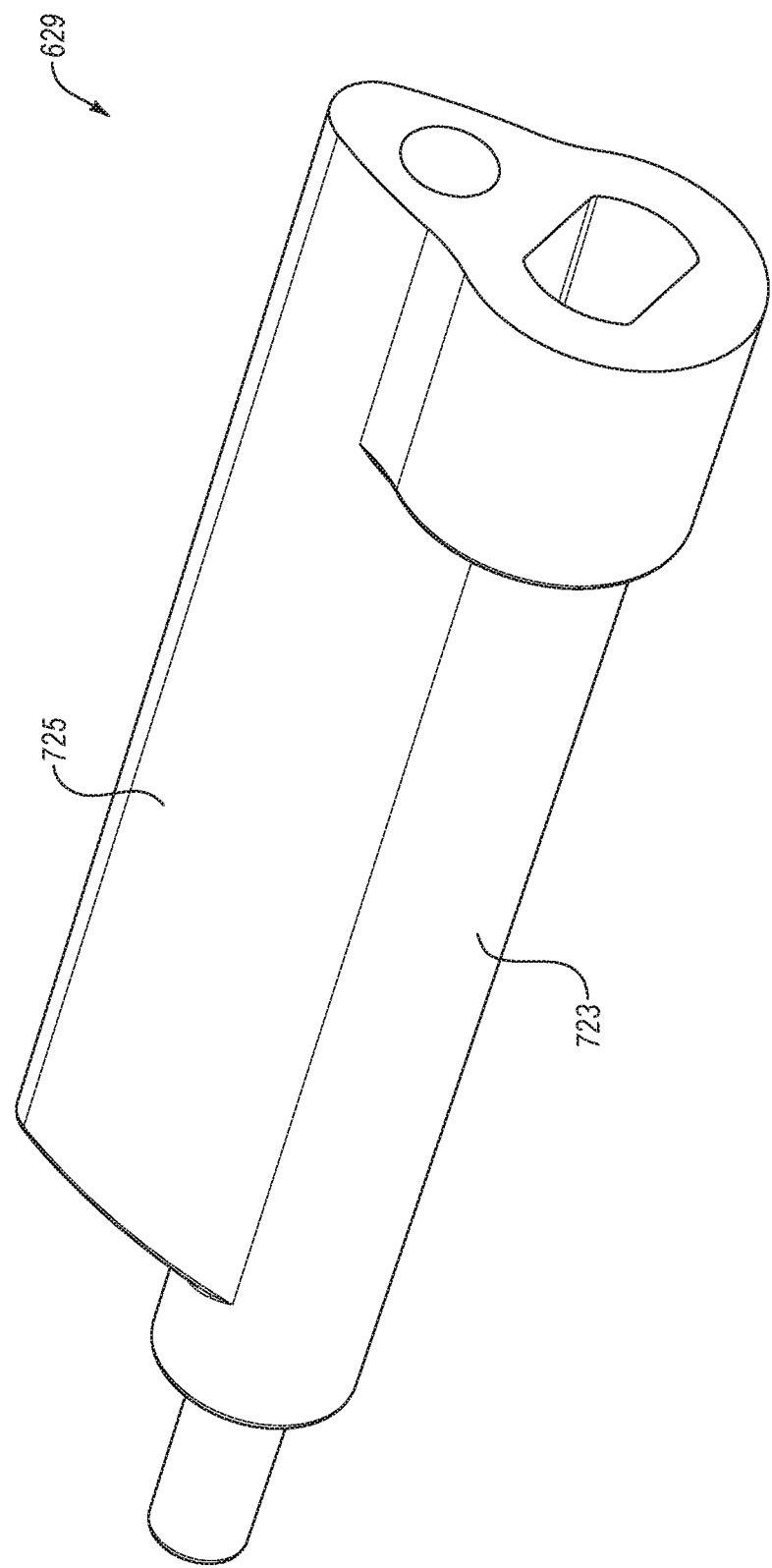
FIG. 7B illustrates a top perspective view of the cam shaft that may be implemented in the radon detection device of FIGS. 4A-4C.

FIG. 7A illustrates a bottom perspective view of the camshaft 629 that may be implemented in the radon detection device 400 of FIGS. 4A-4C. FIG. 7B illustrates a top perspective view of the camshaft 629 that may be implemented in the radon detection device 400 of FIGS. 4A-4C. With combined reference to FIGS. 7A and 7B, the camshaft 629 may rotate relative to an axis. A top portion 725 of the camshaft 629 may extend farther from the axis relative to a bottom portion 733 of the camshaft 629. The camshaft 629 as illustrated in FIG. 7A is in the seal position. Further, the camshaft 629 as illustrated in FIG. 7B is in the open position.

Figure 8:
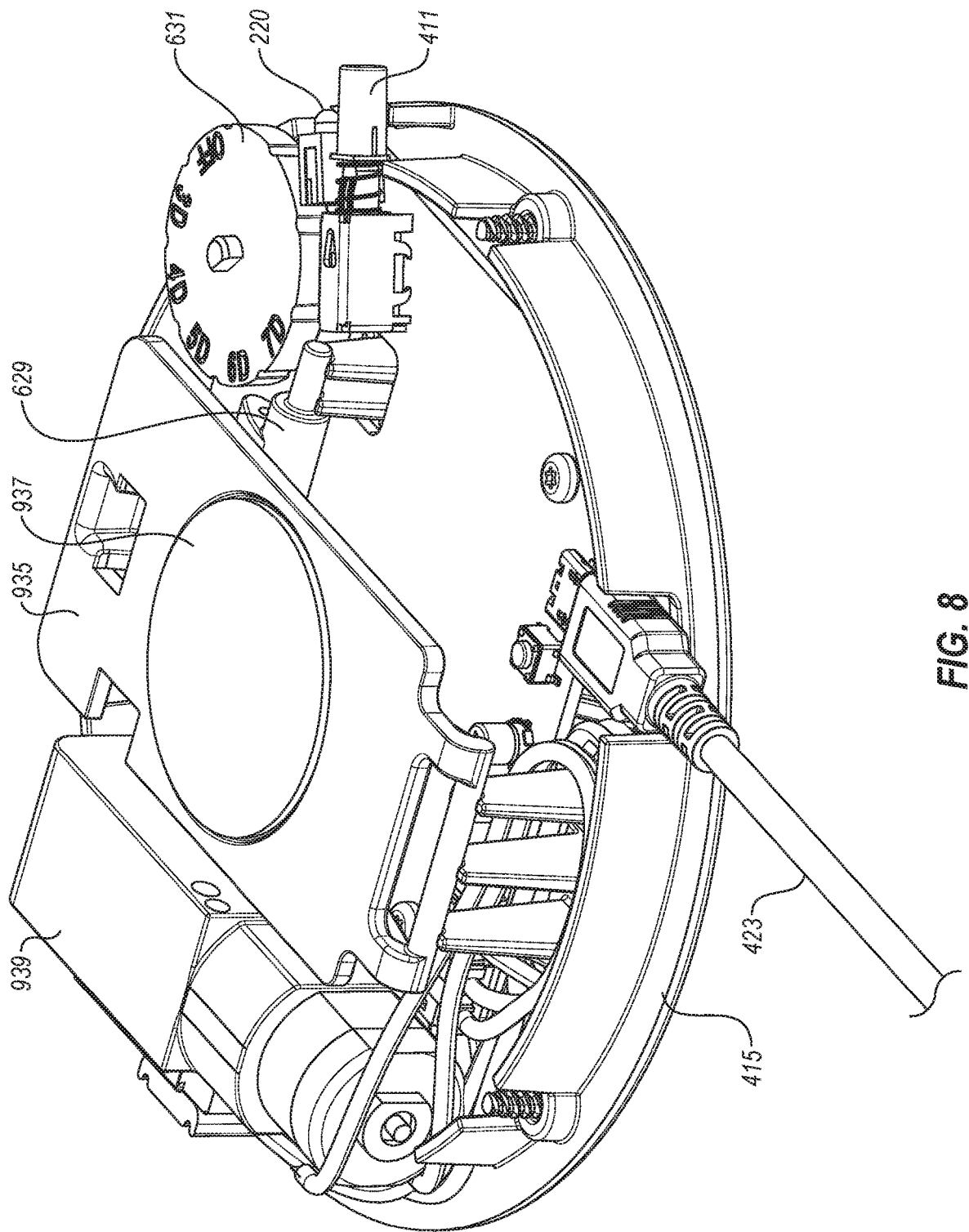
FIG. 8 illustrates a perspective view of the radon detection device of FIGS. 4A-4C with multiple pieces removed to illustrate internal components of the radon detection device.

FIG. 8 illustrates a perspective view of the radon detection device 400 of FIGS. 4A-4C with multiple pieces removed to illustrate internal components of the radon detection device 400. The radon detection device 400 may include a seal support 935, a seal 937, and a motor 939. The motor 939 may be mechanically coupled to the camshaft 629. In addition, the camshaft 629 may be mechanically coupled to the seal support 935. Likewise, the seal support 935 may be mechanically coupled to the seal 937. The seal 937 may be the same as or similar to the seal 112 discussed above in relation to FIGS. 1-3.

The motor 939 may be configured to position the camshaft 629 in the open position or in the seal position. For example, after the activation switch 411 is selected, the motor 939 may receive a first power signal from the electrical components of the radon detection device 400. The motor 939, in response to the first power signal, may cause the camshaft 629 to physically move from the seal position (shown in FIG. 11A) to the open position (shown in FIG. 11B). In addition, the seal support 935, in response to the camshaft 629 moving from the seal position to the open position, may move from a first position (shown in FIG. 11A) to a second position (shown in FIG. 11B). Likewise, the seal 937 may move from a seal position to an open position. The seal 937 moving to the open position may expose the test material 1041 to the ambient air of the external environment.

In addition, after the test period has elapsed, the motor 939 may receive a second power signal from the electrical components of the radon detection device 400. The motor 939, in response to the second power signal, may cause the camshaft 629 to move from the open position to the seal position, which may cause the seal support 935 to move to the first position and the seal 937 to move to the seal position.

In addition, the electrical components of the radon detection device 400 may be configured to automatically delay starting the test period for a period of time (e.g., the electrical components may create a closed housed condition). For example, the electrical components may delay the starting the test period for 12 hours, 24 hours, 36 hours, 72 hours, or any other appropriate amount of time.

Figure 9A:
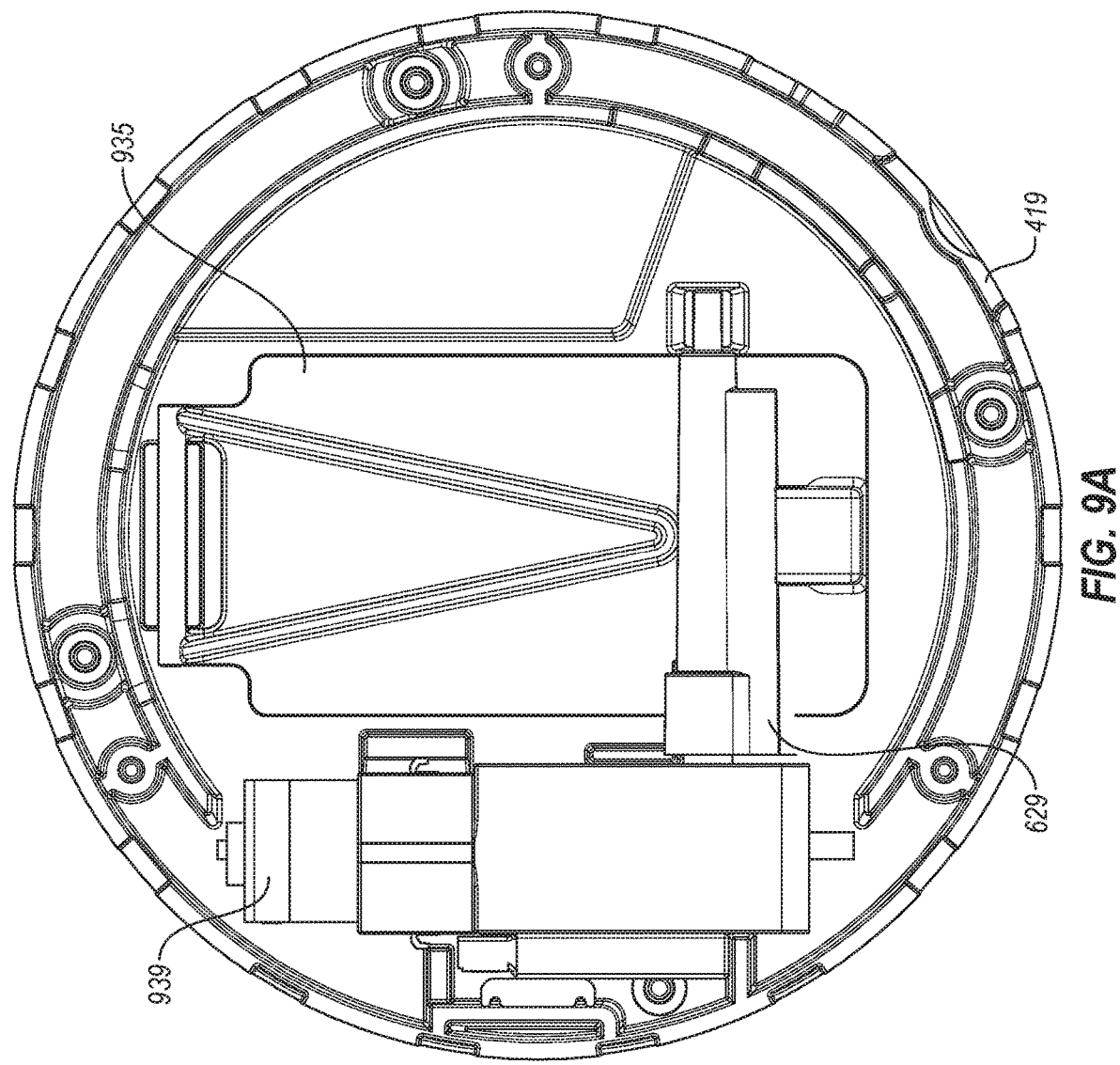
FIG. 9A illustrates a bottom view of the radon detection device of FIGS. 4A-4C with the bottom plate removed.
Figure 9B:
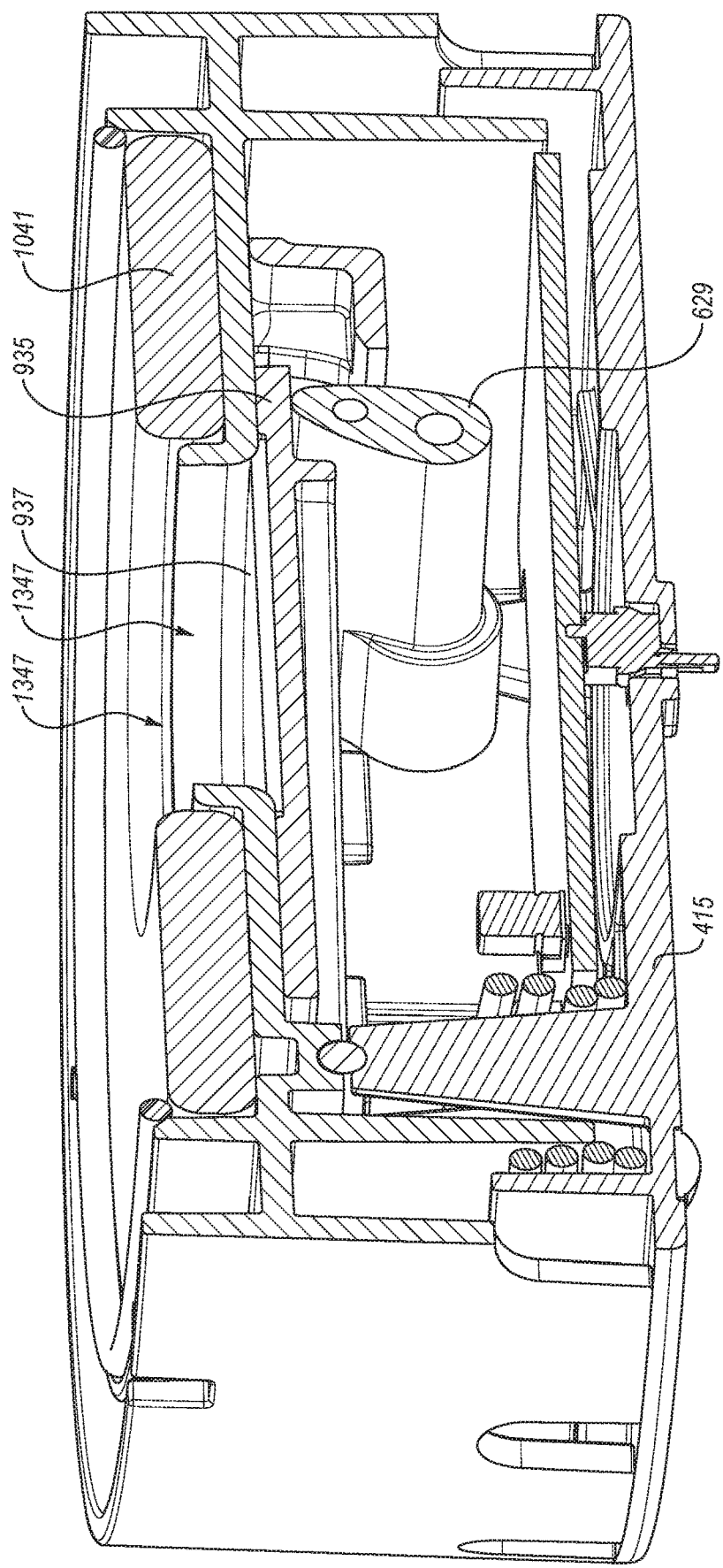
FIG. 9B illustrates a cross-sectional perspective view of the radon detection device of FIGS. 4A-4C with a top plate removed to illustrate internal components of the radon detection device.

FIG. 9A illustrates a bottom view of the radon detection device 400 of FIGS. 4A-4C with the bottom plate 415 removed. FIG. 9B illustrates a cross-sectional perspective view of the radon detection device 400 of FIGS. 4A-4C with the top plate 417 removed to illustrate internal components of the radon detection device 400. With combined reference to FIGS. 10A and 10B, the radon detection device 400 may include an O-ring 1345 and the test material 1041. The test material 1041 may be the same as or similar to the test material 110 discussed above in relation FIGS. 1-3. The test material 1041 may define a material opening 1043. In addition, the sidewall portion 419 may define an opening 1347. The opening 1347 and the material opening 1043 may operate the same as or similar to the vent 106 discussed above in relation to FIGS. 1-3.

Figure 10A:
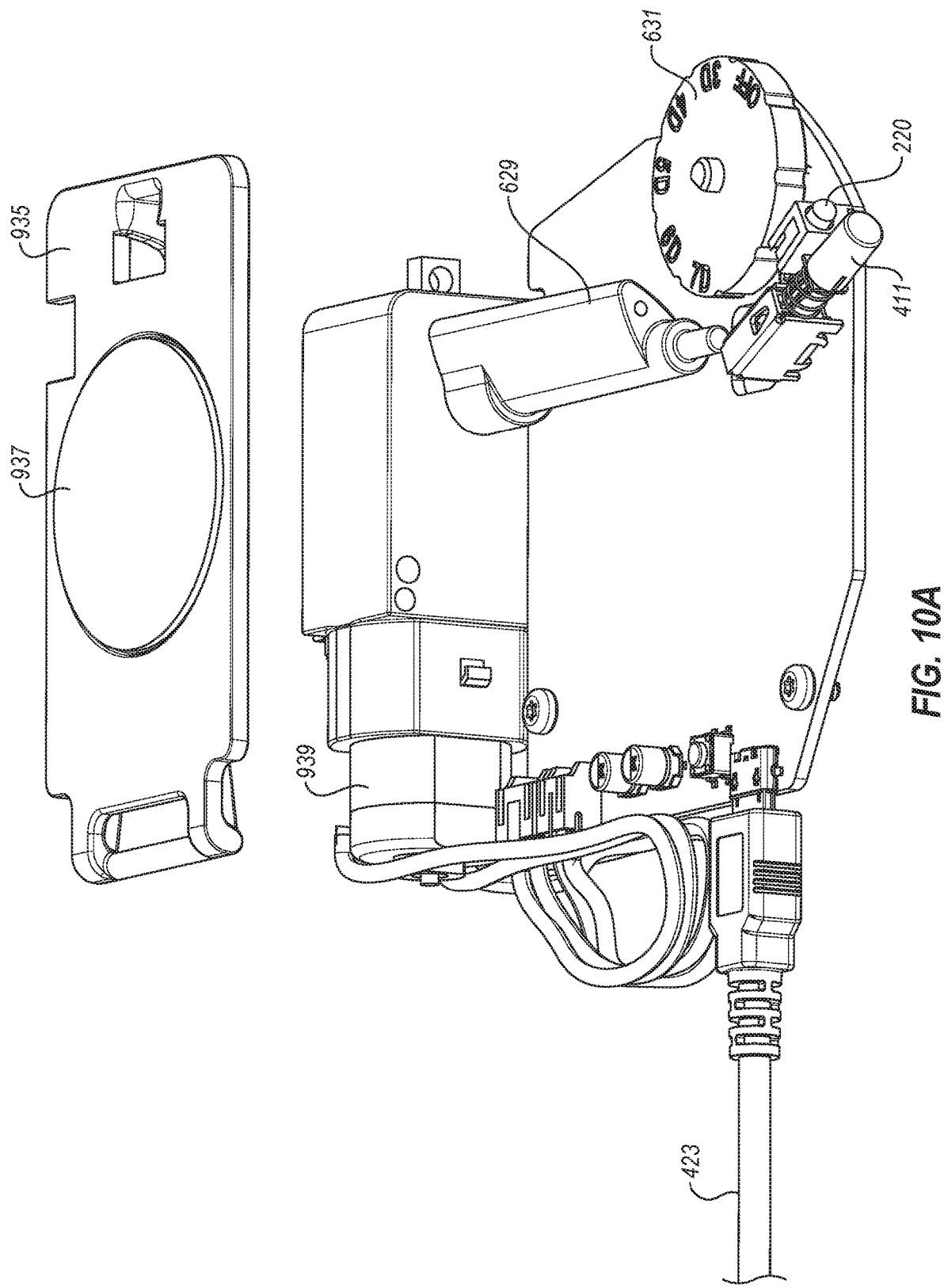
FIG. 10A illustrates a partial exploded view of internal components that may be implemented in the radon detection device of FIGS. 4A-4C.
Figure 10B:
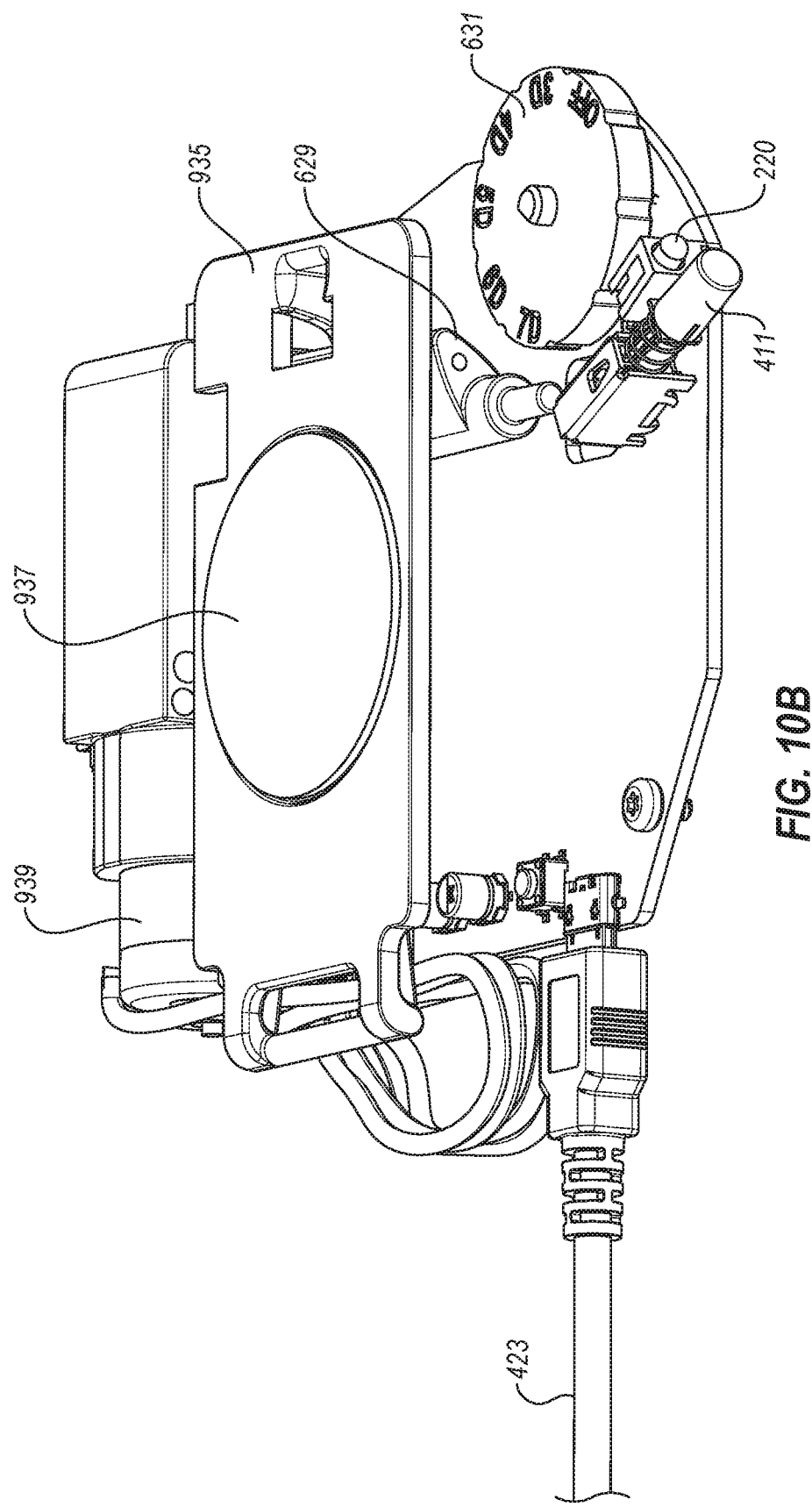
FIG. 10B illustrates a perspective view of internal components that may be implemented in the radon detection device of FIGS. 4A-4C.

FIG. 10A illustrates a partial exploded view of internal components that may be implemented in the radon detection device 400 of FIGS. 4A-4C. FIG. 10B illustrates a perspective view of internal components that may be implemented in the radon detection device 400 of FIGS. 4A-4C.

Figure 11A:
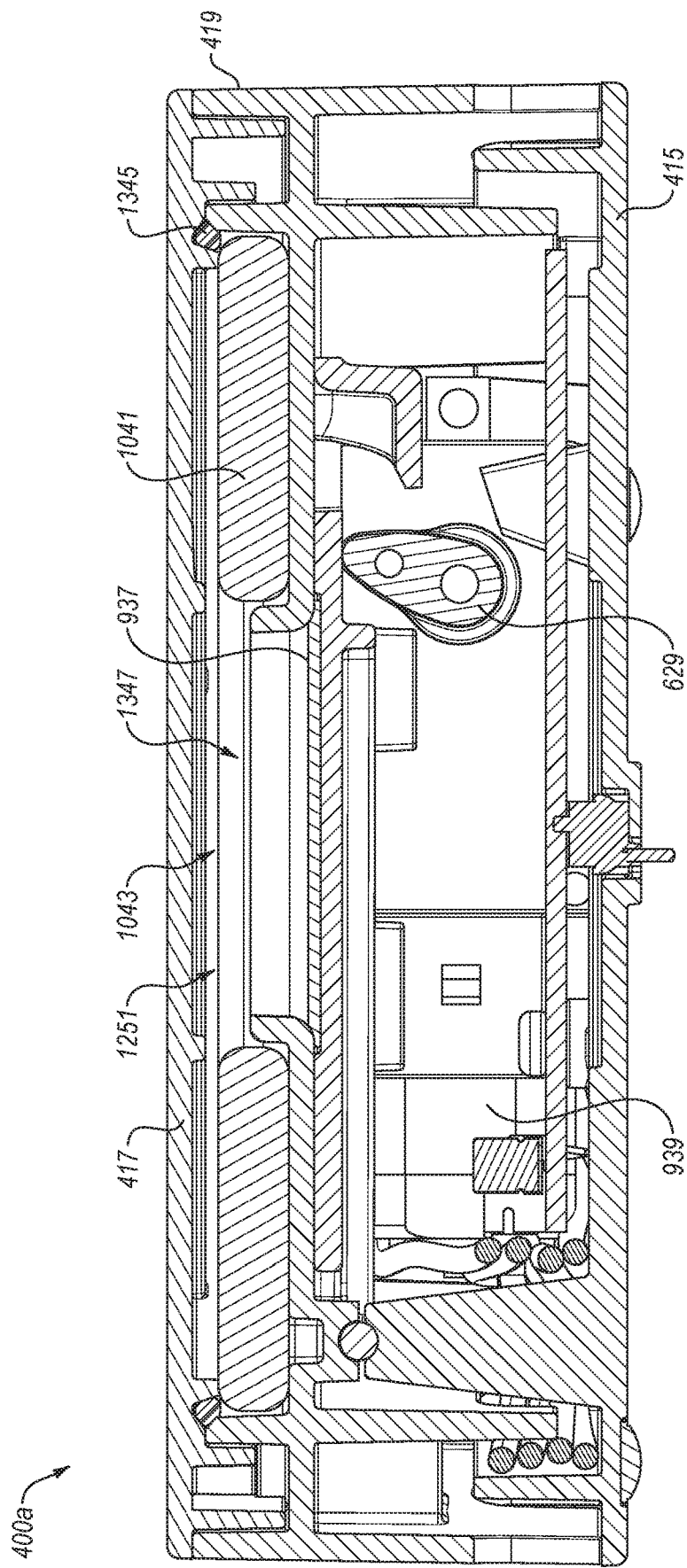
FIG. 11A illustrates a cross sectional view of the radon detection device of FIGS. 4A-4C in an open configuration.
Figure 11B:
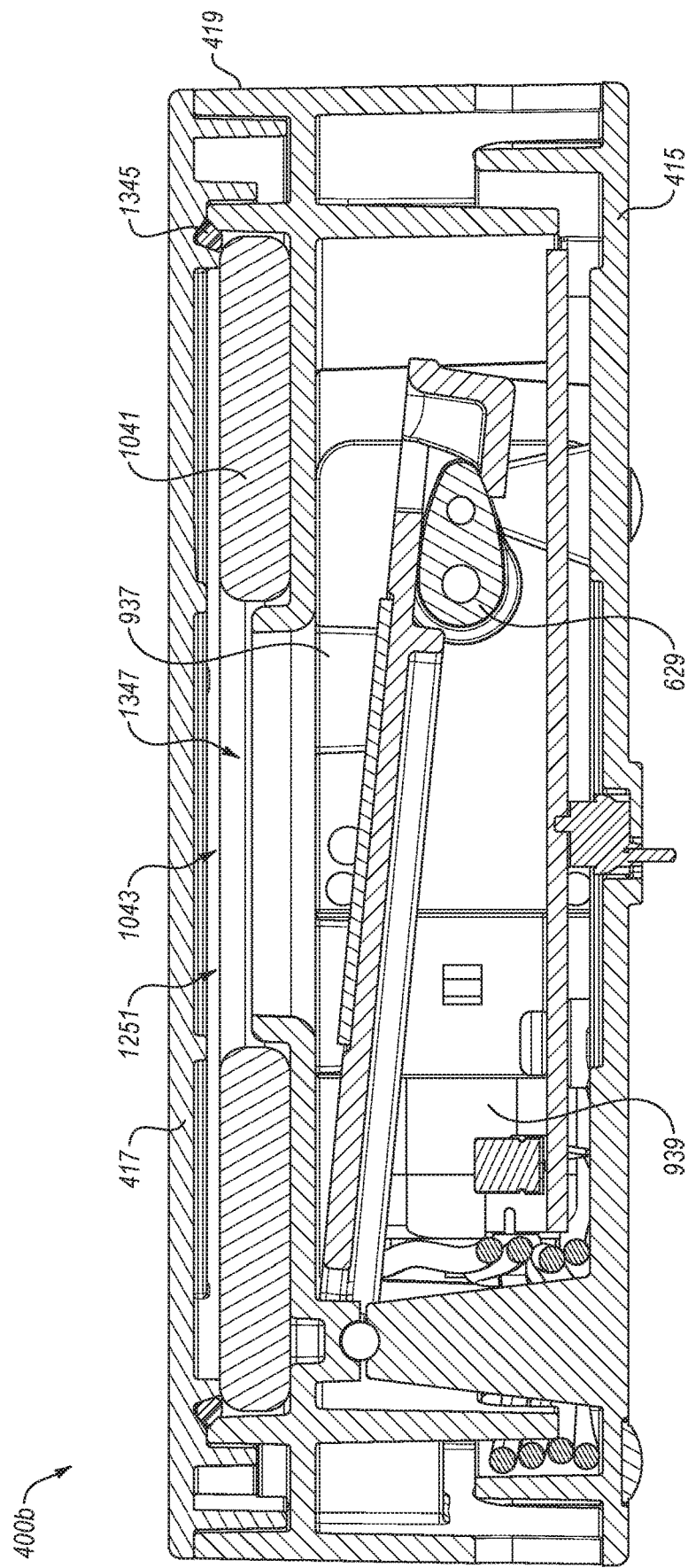
FIG. 11B illustrates a cross sectional view of the radon detection device of FIGS. 4A-4C in a sealed configuration.

FIG. 11A illustrates a cross sectional view of the radon detection device 400 of FIGS. 4A-4C in a sealed configuration 400a. FIG. 11B illustrates a cross sectional view of the radon detection device 400 of FIGS. 4A-4C in an open configuration 400b. In the sealed configuration 400a, the camshaft 629 may be positioned such that the seal support 935 is pushed towards the top plate 417 by the camshaft 629, which may cause the seal 937 to physically contact the sidewall portion 419. The seal 937 contacting the sidewall portion 419 may seal the material opening 1043 and the opening 1347. In the sealed configuration 400a, the seal 937, the sidewall portion 419, and the O-ring 1345 may define the chamber 1251. The chamber 1251, in the sealed configuration 400a, may be hermetically sealed to prevent the test material 1041 from being exposed to the ambient air in the external environment.

In the open configuration 400b, the camshaft 629 may be positioned such that the seal support may move towards the bottom plate 415, which may cause the seal 937 to move away from the opening 1347 and the material opening 1043. In the open configuration, the chamber 1251 may not be hermetically sealed and the test material 1041 may be exposed to the ambient air in the external environment. For example, the ambient air may pass through environmental openings 413 and may enter the chamber 1251 via the opening 1347 and the material opening 1043. As discussed elsewhere in the present disclosure, after a testing period, the camshaft 629 may be moved to first position and the radon detection device 400 may be in the sealed configuration 400a.

Figure 12A:
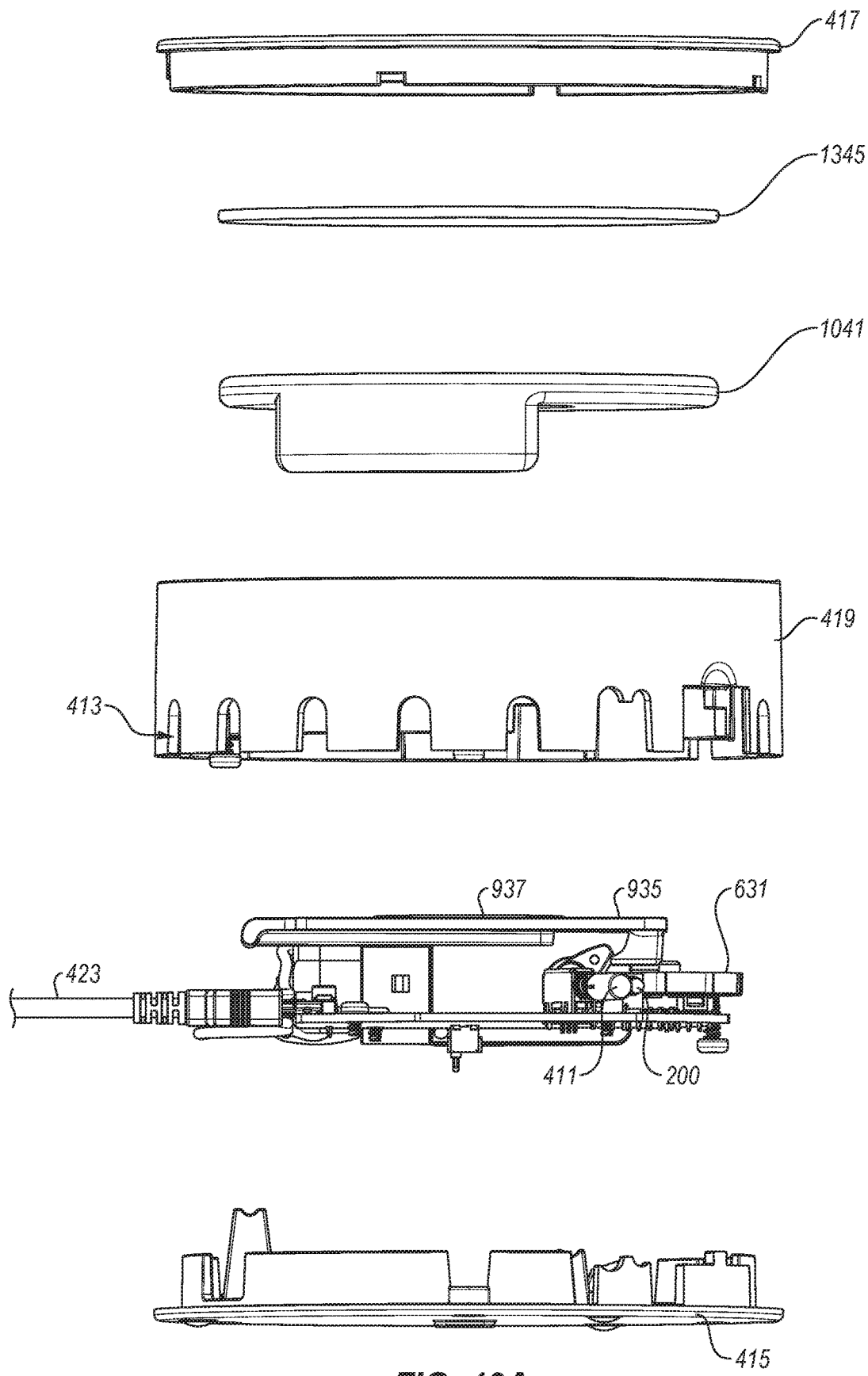
FIG. 12A illustrates an exploded side view of the radon detection device of FIGS. 4A-4C.
Figure 12B:
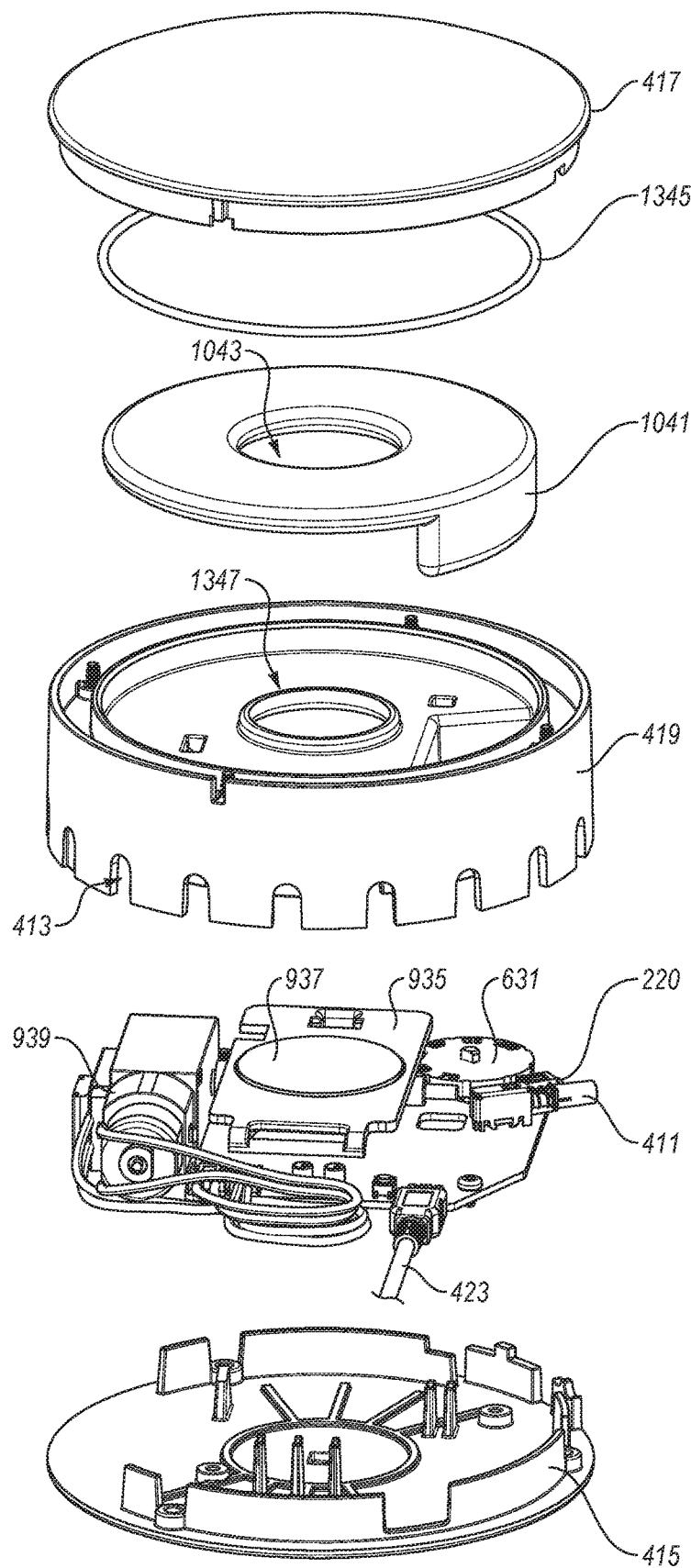
FIG. 12B illustrates a first exploded perspective view of the radon detection device of FIGS. 4A-4C.
Figure 12C:
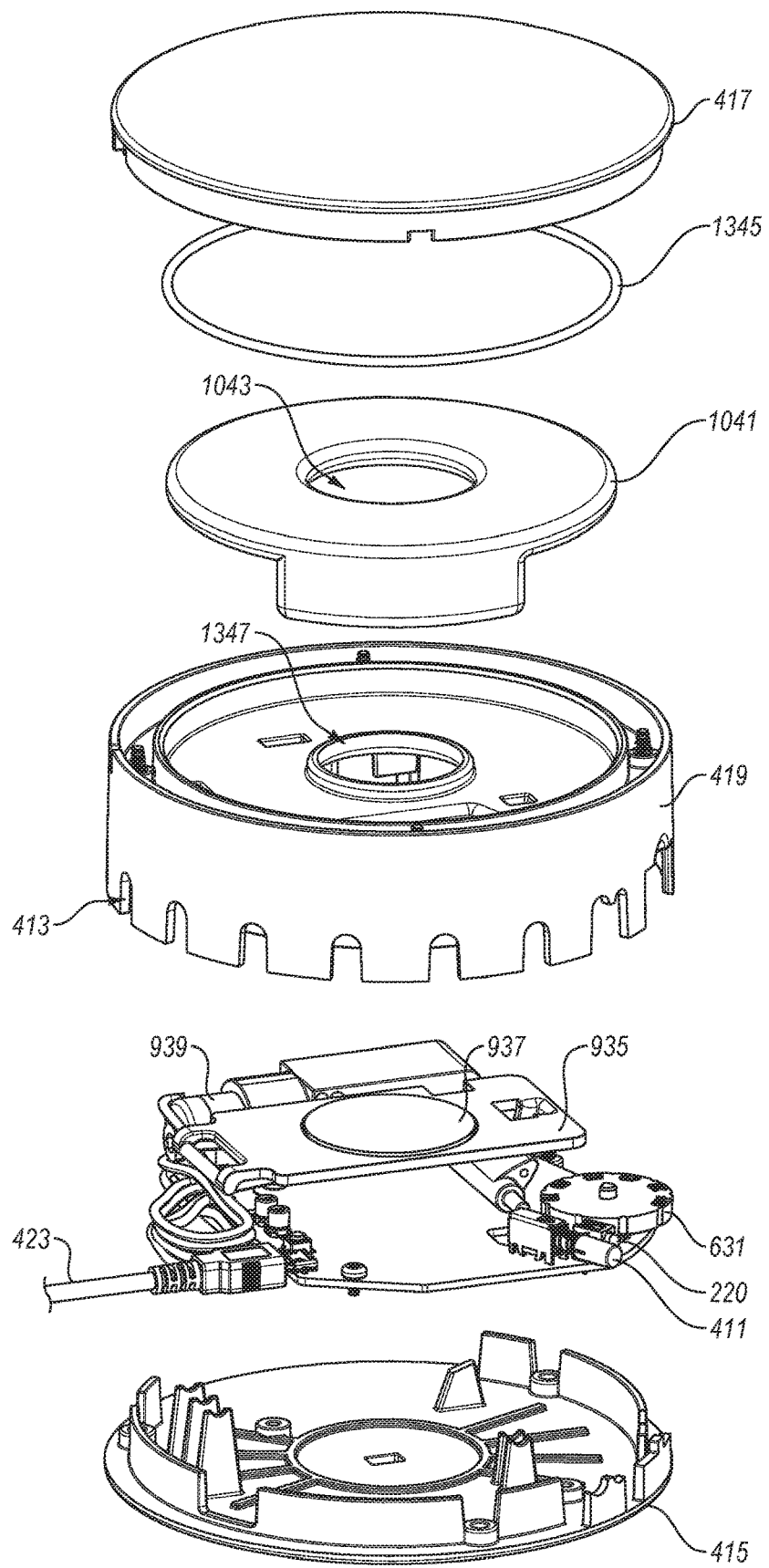
FIG. 12C illustrates a second exploded perspective view of the radon detection device of FIGS. 4A-4C.
Figure 12D:
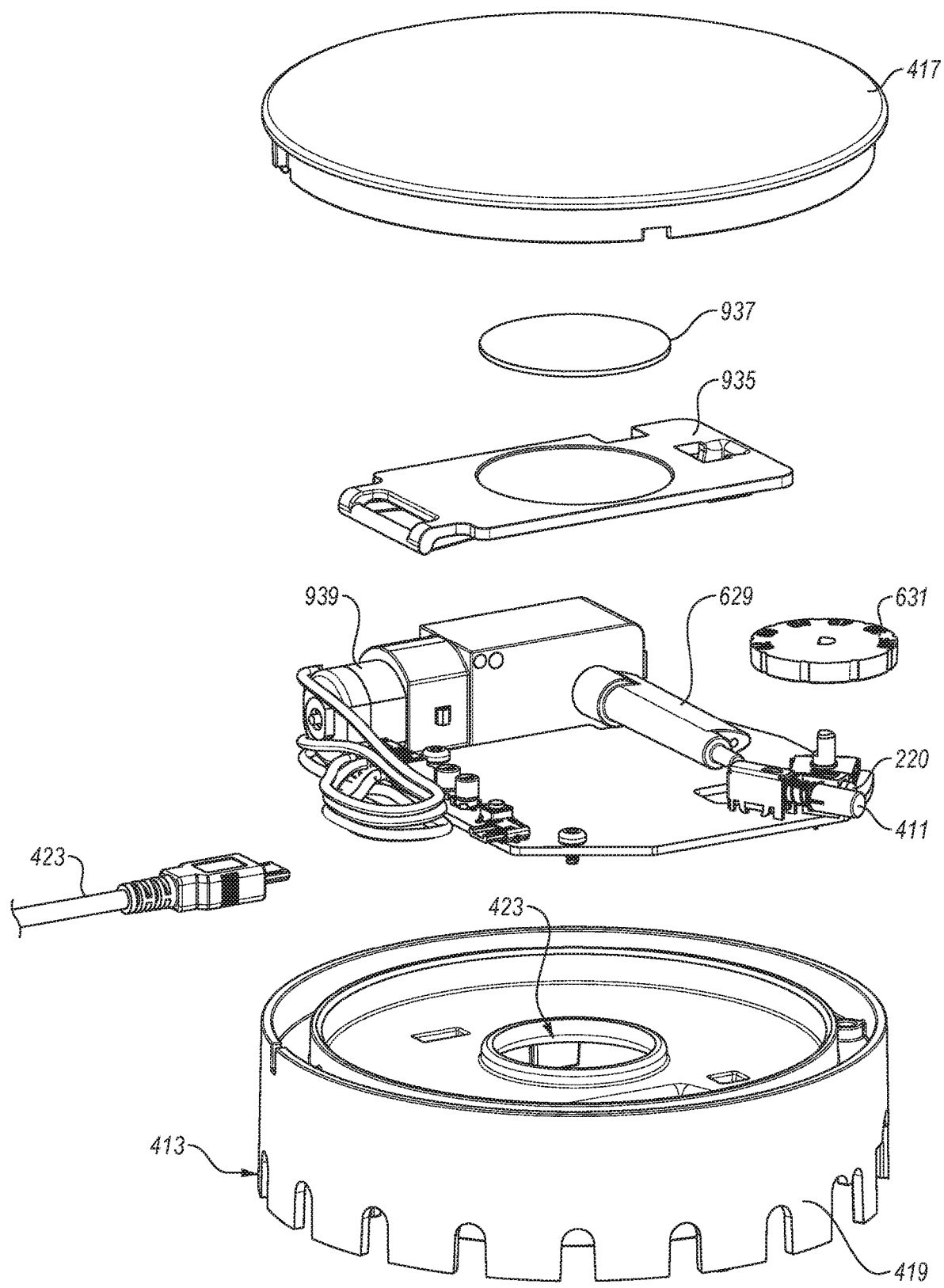
FIG. 12D illustrates a third exploded perspective view of the radon detection device of FIGS. 4A-4C.
Figure 14:
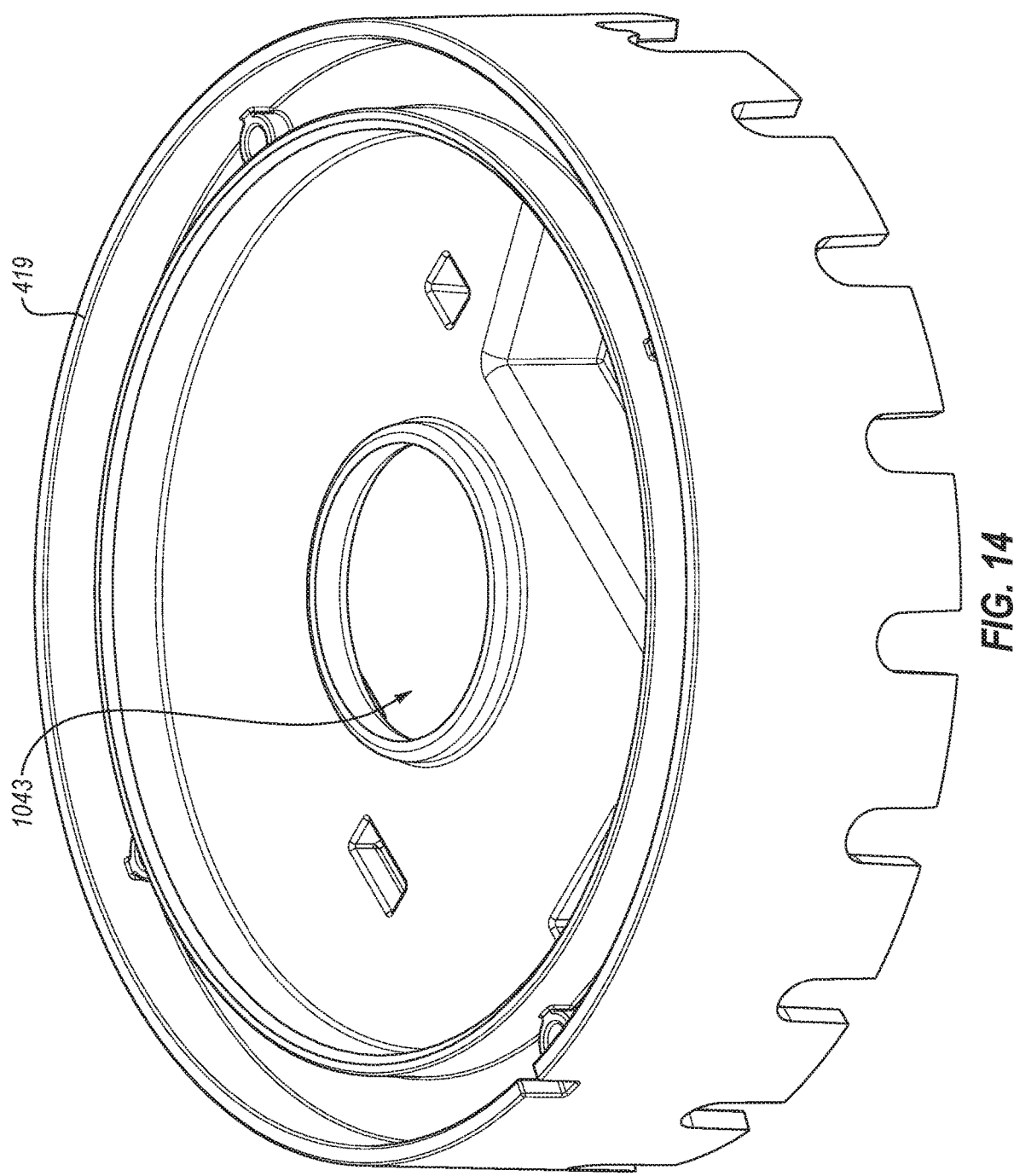
FIG. 14 illustrates a perspective view of the sidewall portion that may be implemented in the radon detection device of FIGS. 4A-4C.

FIG. 12A illustrates an exploded side view of the radon detection device 400 of FIGS. 4A-4C. FIG. 12B illustrates a first exploded perspective view of the radon detection device 400 of FIGS. 4A-4C. FIG. 12C illustrates a second exploded perspective view of the radon detection device 400 of FIGS. 4A-4C. FIG. 12D illustrates a third exploded perspective view of the radon detection device 400 of FIGS. 4A-4C. FIG. 13 illustrates a perspective view of the test material 1041 that may be implemented in the radon detection device 400 of FIGS. 4A-4C. FIG. 14 illustrates a perspective view of the sidewall portion 419 that may be implemented in the radon detection device 400 of FIGS. 4A-4C.

Figure 15:
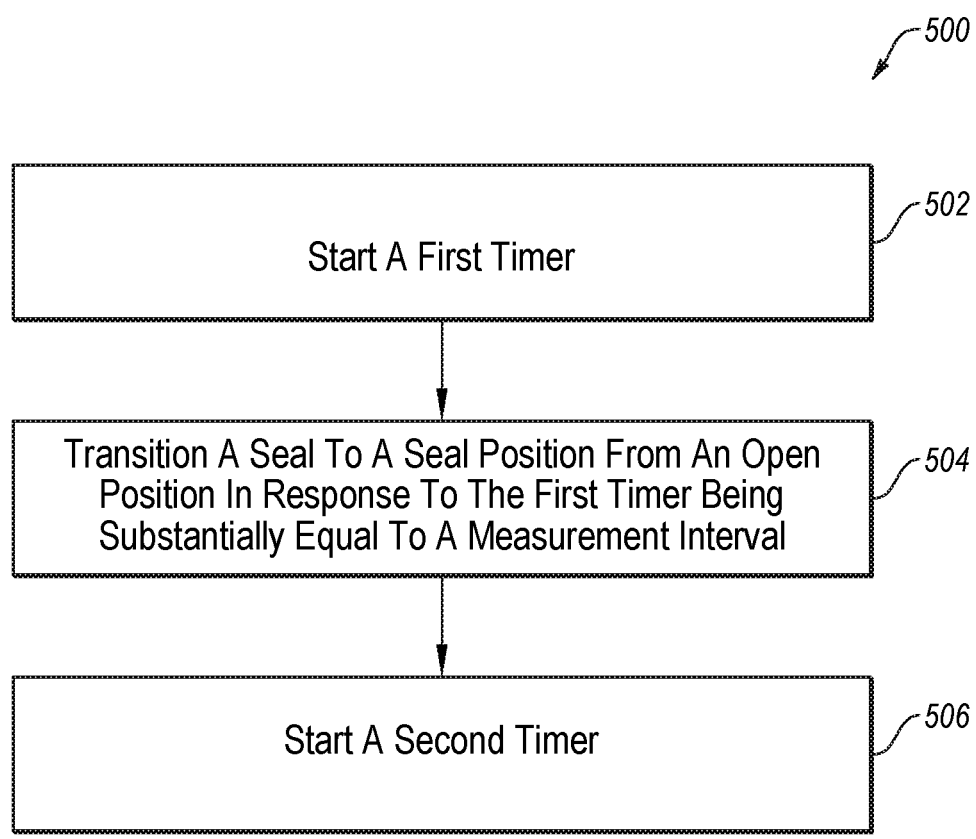
FIG. 15 is a flowchart of an example method of detecting radon.

FIG. 15 is a flowchart of an example method 500 of detecting radon. The method 500 may be performed via a radon detection device generally corresponding to the radon detection device 100 of FIG. 1, the radon detection device 200 of FIG. 2, the radon detection device 300 of FIG. 3, or the radon detection device 400 of FIGS. 4A-4C.

The method 500 may begin at block 502 by starting a first timer. The first timer may be started at a clock circuit generally corresponding to the clock circuit 116 of FIGS. 1-3. The first timer may be started in response to a first triggering action. In some embodiments, the first triggering action may include a switch transitioning to a second position from a first position. Alternately or additionally, the first triggering action may occur a predetermined length of time following a preliminary action. The switch may generally correspond to the switch 114 of FIGS. 1-3 or the switch 411 of FIGS. 4A-4C, 5C, 6, 8, 10A-10B, and 12A-12D. In some configurations, the switch may remain locked in the second position from the start of the first timer until the first timer is substantially equal to the measurement interval. Alternately or additionally, the method 500 may further include performing an alarm in response to the switch being moved out of the second position before the first timer is substantially equal to the measurement interval.

The method 500 may continue at block 504 by transitioning a seal to a seal position from an open position. The seal may generally correspond to the seal 112 of FIGS. 1-3 or the seal 937 of FIGS. 8, 9B-12D. The seal may be transitioned to the seal position from the open position in response to the first timer being substantially equal to a measurement interval. The open position may facilitate the introduction of ambient air to a vent of the radon detection device. The ambient air may generally correspond to the ambient air 108 of FIGS. 1-3. The vent may generally correspond to the vent 106 of FIGS. 1-3 or the opening 1347 of FIGS. 9B, 11A-11B, and 12B-12D. The seal position may discourage introduction of the ambient air to the vent. The vent may be in fluid communication with a test material located within the radon measurement device. The test material may generally correspond to the test material 110 of FIGS. 1-3 or the test material 1041 of FIGS. 9B, 11A-12C, and 13. The test material may be configured to collect radon from the ambient air introduced to the radon detection device. In some embodiments, transitioning the seal to the seal position from the open position may be performed by an actuator. The actuator may generally correspond to the actuator 322 of FIG. 3 or the motor 939 of FIGS. 8, 9A, 10A-11B, and 12B-12D.

The method 500 may continue at block 506 by starting a second timer in response to the seal transitioning from the open position to the seal position. The seal may remain in the sealed position following the transition from the open position to the sealed position.

In some embodiments, the method 500 may further include transitioning the seal to the open position from the seal position in response to the first triggering action.

Alternately or additionally, the method 500 may further include determining an Average Radon Level based on the radon collected from the ambient air by the test material. In some instances, the method 500 may further continue by determining a margin of error associated with the Average Radon Level based on a value of the second timer.

Alternately or additionally, the method may further include generating tamper data in response to the radon detection device being moved from an initial position before the first timer is substantially equal to the measurement interval. The initial position may be associated with a position of the radon detection device in an environment at a time that the first trigger action occurred.

One skilled in the art will appreciate that, for this and other procedures and methods disclosed in the present disclosure, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the disclosed embodiments.

Terms used in the present disclosure and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one," "one or more," "at least one of the following," and "one or more of the following" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

Additionally, the use of the terms "first," "second," "third," etc., are not necessarily used in the present disclosure to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

The scope of the present invention serves as a solution to the current problems in radon measurement technologies. Examples below are problems and solutions made by the one or more embodiments described in the present disclosure.

All examples and conditional language recited in the present disclosure are intended for pedagogical objects to aid the reader in understanding the example embodiments and the concepts contributed by the inventor to furthering the art, and are to be construed as being without limitation to such specifically-recited examples and conditions.

What is claimed is:

1. A method of detecting radon, comprising:
   imposing, by a user, a preliminary action on a radon detection device, the preliminary action preparing an environment in which the radon detection device is configured to operate;
   imposing, by the radon detection device without input by the user, a first triggering action on a switch a predetermined time after the preliminary action is imposed on the radon detection device;
   transitioning a seal of the radon detection device to an open position from a seal position in response to the first triggering action on the switch, the open position facilitating introduction of ambient air to a vent of the radon detection device and the seal position discouraging introduction of the ambient air to the vent, wherein the vent is in fluid communication with a test material located within the radon detection device, the test material being configured to collect radon from the ambient air introduced to the radon detection device;
   imposing, by the radon detection device without input by the user, a second triggering action on the switch that transitions the switch of the radon detection device to a lock position from the open position in response to the second triggering action on the switch, the lock position preventing the switch from transitioning to the seal position from the open position for an amount of time;
   starting a first timer at a clock circuit of a radon detection device in response to and concurrent to the first triggering action;
   performing an alarm in response to the switch being moved out of the open position before the first timer is substantially equal to the measurement interval;
   imposing, by the radon detection device without input by the user, a third triggering action that transitions the seal of the radon detection device to the seal position from the open position in response to the first timer being substantially equal to the measurement interval, the switch being configured to prevent the seal of the radon detection device from transitioning from the seal position back to the open position after the third triggering action is imposed; and
   starting a second timer and stopping the first timer in response to the third triggering action, wherein the seal remains in the sealed position following the transition from the open position to the sealed position.

2. The method of claim 1, further comprising determining an Average Radon Level based on the radon collected from the ambient air by the test material.

3. The method of claim 2, further comprising determining a margin of error associated with the Average Radon Level, the margin of error determined based on a value of the second timer.

4. The method of claim 1, wherein the transitioning the seal of the radon detection device to the seal position from the open position is performed by way of an actuator.

5. The method of claim 1, wherein the amount of time that the switch remains in the lock position is from the start of the first timer until the first timer is substantially equal to the measurement interval.

6. The method of claim 1, further comprising performing an alarm in response to the switch being in the seal position in response to the first timer being substantially equal to the measurement interval.

7. The method of claim 1, further comprising generating tamper data in response to the radon detection device being moved from an initial position before the first timer is substantially equal to the measurement interval, the initial position being associated with a position of the radon detection device in an environment at a time that the first trigger action occurred.

8. A radon detection device, comprising:
   a housing that defines a radon measurement device and includes a vent that is configured to introduce ambient air into the radon measurement device;
   test material disposed in the radon measurement device, the test material being configured to collect radon from the ambient air introduced into the radon measurement device;
   a seal positioned proximate the vent, the seal configured to transition between a seal position and an open position, in the seal position, the seal is configured to prevent introduction of the ambient air into the radon measurement device and in the open position, the seal is configured to permit introduction of the ambient air into the radon measurement device, wherein the seal is configured to:
     transition from the seal position to the open position in response to a first triggering action without input from a user;
     transition from the open position to a lock position in response to a second triggering action without input from the user; and
     transition from the lock position to the seal position in response to a third triggering action without input from the user in which the third triggering action transitions the seal of the radon detection device to the seal position from the open position, a switch being configured to prevent the seal of the radon detection device from transitioning from the seal position back to the open position after the third triggering action is imposed;
   the switch mechanically coupled to the seal, the switch being configured to transition between a first position, a second position, and the lock position, in the first position, the switch is configured to cause the seal to be in the seal position, in the second position, the switch is configured to cause the seal to be in the open position, and in the lock position, the switch is configured to prevent the seal from transitioning from the open position to the seal position prior to a first time period being substantially equal to a measurement interval and prevent the seal from transitioning from the seal position to the open position after the third triggering action is imposed;

an alarm circuit communicatively coupled to the switch and a clock circuit, the alarm being configured to determine whether the switch is in the lock position, wherein the alarm circuit is configured to determine whether the switch is in the lock position responsive to the first time period being substantially equal to an alarm period; and a clock circuit communicatively coupled to the switch and the seal, the clock circuit being configured to determine the first time period, the first time period being representative of a period of time since the seal transitioned to the open position from the seal position.

9. The radon detection device of claim 8, wherein:

responsive to the first time period being substantially equal to the measurement interval, the switch is configured to transition from the lock position to the first position to cause the seal to transition to the seal position to prevent further introduction of the ambient air into the radon measurement device; and responsive to the seal transitioning to the seal position from the open position, the clock circuit is further configured to determine a second time period, the second time period being representative of a period of time since the seal transitioned to the seal position from the open position.

10. The radon detection device of claim 8, wherein responsive to the switch not being in the lock position, the alarm circuit is configured to generate at least one of a visual alarm and an audible alarm.

11. The radon detection device of claim 8, wherein the seal is configured to be locked in the seal position after transitioning to the seal position from the open position.

12. The radon detection device of claim 8, further comprising a notification circuit communicatively coupled to the clock circuit and to the switch, wherein responsive to the first time period not being substantially equal to the measurement interval and the switch being in the lock position, the notification circuit is configured to generate a visual indicator indicating that the first time period is not substantially equal to the measurement and that the switch is in the lock position.

13. The radon detection device of claim 8, wherein the measurement interval is configurable by a user of the radon detection device.

14. The radon detection device of claim 8, wherein the switch comprises:

an actuator mechanically coupled to the seal; and a retention device mechanically coupled to the actuator and communicatively coupled to the clock circuit, wherein:

the actuator is configured to transition between the first position, the second position, and the lock position to cause the seal to transition between the seal position and the open position and the retention device is configured to prevent the actuator from transitioning from the lock position to the first position prior to the first time period being substantially equal to the measurement interval and the retention device is configured to automatically cause the actuator to transition to the first position to cause the seal to transition to the seal position from the open position when the first time period is substantially equal to the measurement interval.

15. The radon detection device of claim 14, further comprising an anti-tamper device communicatively coupled to the actuator, the anti-tamper device configured to determine whether the actuator was caused to move from the lock position to the first position by means other than the retention device.

16. The radon detection device of claim 8, further comprising:

a temperature sensor disposed in the radon measurement device, the temperature sensor configured to determine a temperature of the ambient air introduced into the radon measurement device; and a humidity sensor disposed in the radon measurement device, the humidity sensor configured to determine a humidity level of the ambient air introduced into the radon measurement device.

17. The radon detection device of claim 8, wherein the seal comprises at least one of a spring loaded gasket and a diaphragm.

* * * * *